US011256033B2

(12) United States Patent
Cai

(10) Patent No.: US 11,256,033 B2
(45) Date of Patent: Feb. 22, 2022

(54) TWO-FILTER LIGHT DETECTION DEVICES AND METHODS RELATED TO SAME

(71) Applicant: Illumina, Inc., San Diego, CA (US)

(72) Inventor: Xiuyu Cai, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 15/929,503

(22) Filed: May 6, 2020

(65) Prior Publication Data

US 2020/0264376 A1 Aug. 20, 2020

Related U.S. Application Data

(63) Continuation of application No. 16/208,949, filed on Dec. 4, 2018, now Pat. No. 10,649,145.

(Continued)

(30) Foreign Application Priority Data

Mar. 20, 2018 (NL) ..................................... 2020625

(51) Int. Cl.
G02B 6/26 (2006.01)
G02B 6/293 (2006.01)
(Continued)

(52) U.S. Cl.
CPC ..... *G02B 6/29368* (2013.01); *G01N 21/6454* (2013.01); *G01N 33/48* (2013.01);
(Continued)

(58) Field of Classification Search
CPC .... G02B 6/29368; G02B 5/20; G02B 6/0026; G02B 5/22; G02B 6/4215; G02B 6/0008;
(Continued)

(56) References Cited

U.S. PATENT DOCUMENTS

| 5,846,708 A | 12/1998 | Hollis et al. |
| 6,030,883 A | 2/2000 | Nishimoto et al. |

(Continued)

FOREIGN PATENT DOCUMENTS

| CL | 201903778 | 7/2020 |
| CL | 201903779 | 7/2020 |

(Continued)

OTHER PUBLICATIONS

Hong, et al., "A fully integrated CMOS fluorescence biosensor with on-chip nanophotonic filter" Symposium on VLSI Circuits (VLSI Circuits), Jun. 17-19, 2015.

(Continued)

*Primary Examiner* — Ellen E Kim
(74) *Attorney, Agent, or Firm* — Marshall, Gerstein & Borun LLP

(57) ABSTRACT

Light detection devices and corresponding methods are provided. The devices include a reaction structure to contain a reaction solution and at least one reaction site that generates light emissions in response to incident excitation light after treatment with the reaction solution. The devices also include a plurality of light sensors and device circuitry. The devices further include a plurality of light guides extending toward at least one corresponding light sensor from input regions that receive the excitation light and the light emissions from at least one corresponding reaction recess. The light guides comprise a first filter region that filters the excitation light and permits the light emissions of a first wavelength to pass to the at least one corresponding light sensor, and a second filter region that filters the excitation light and the permits light emissions of a second wavelength to pass to the at least one corresponding light sensor.

20 Claims, 13 Drawing Sheets

Related U.S. Application Data

(60) Provisional application No. 62/609,903, filed on Dec. 22, 2017.

(51) Int. Cl.

| | | |
|---|---|---|
| *G01N 21/64* | (2006.01) | |
| *G01N 33/48* | (2006.01) | |
| *G02B 5/20* | (2006.01) | |
| *F21V 8/00* | (2006.01) | |
| *G01N 21/03* | (2006.01) | |

(52) U.S. Cl.
CPC .............. *G02B 5/20* (2013.01); *G02B 6/0026* (2013.01); *G01N 2021/0325* (2013.01)

(58) Field of Classification Search
CPC .............. G01N 21/6454; G01N 33/48; G01N 2021/0325; G01N 2021/6471; G01N 21/6428; G01N 2021/6432; G01N 2021/6439; H01L 27/14643; H01L 27/146; G01J 2001/448
See application file for complete search history.

(56) References Cited

U.S. PATENT DOCUMENTS

| | | | |
|---|---|---|---|
| 6,527,709 | B2 | 3/2003 | Matsumoto |
| 8,906,320 | B1 | 12/2014 | Eltoukhy et al. |
| 9,373,732 | B2 | 6/2016 | Velichko et al. |
| 9,704,898 | B2 | 7/2017 | Chung et al. |
| 9,842,870 | B2 | 12/2017 | Chung et al. |
| 10,883,937 | B2 * | 1/2021 | Fung ................ H01L 27/14625 |
| 10,955,343 | B2 | 3/2021 | Cai et al. |
| 2005/0025499 | A1 | 2/2005 | Pattie |
| 2005/0244870 | A1 | 11/2005 | Chee et al. |
| 2007/0023754 | A1 | 2/2007 | Zhong et al. |
| 2008/0132072 | A1 | 6/2008 | Letz et al. |
| 2010/0065726 | A1 | 3/2010 | Zhong et al. |
| 2010/0121022 | A1 | 5/2010 | Musa et al. |
| 2010/0204064 | A1 | 8/2010 | Cho |
| 2012/0010395 | A1 | 1/2012 | Skrzypczynski et al. |
| 2015/0005447 | A1 | 1/2015 | Berti et al. |
| 2015/0079596 | A1 | 3/2015 | Eltoukhy et al. |
| 2016/0061740 | A1 * | 3/2016 | Grot ........................ G02B 6/132 506/16 |
| 2016/0334334 | A1 | 11/2016 | Saxena et al. |
| 2016/0356715 | A1 | 12/2016 | Zhong et al. |
| 2017/0016830 | A1 | 1/2017 | Chung et al. |
| 2017/0102530 | A1 * | 4/2017 | Chang ................ G02B 21/0008 |
| 2019/0198553 | A1 * | 6/2019 | Cai .................... H01L 27/14636 |
| 2020/0147595 | A1 | 5/2020 | Kraft |

FOREIGN PATENT DOCUMENTS

| | | |
|---|---|---|
| CN | 101493411 A | 7/2009 |
| CN | 103325804 A | 9/2013 |
| CN | 104000600 | 8/2014 |
| CN | 105980832 A | 9/2016 |
| CN | 106353285 A | 1/2017 |
| CN | 209894700 U | 1/2020 |
| EP | 2 221 606 A2 | 8/2010 |
| JP | H09-022028 A | 1/1997 |
| JP | H09-284473 A | 10/1997 |
| JP | H10-051589 A | 2/1998 |
| JP | 2001257835 | 9/2001 |
| JP | 2006-025427 A | 1/2006 |
| JP | 2012-000811 A | 1/2012 |
| JP | 2017504789 | 2/2017 |
| JP | 2019-571232 A | 2/2021 |
| WO | WO-00/036445 A1 | 6/2000 |
| WO | WO-2005/054826 A1 | 6/2005 |
| WO | WO-2009/081325 A1 | 7/2009 |
| WO | 2016/168996 | 10/2016 |
| WO | WO-2016/208299 A1 | 12/2016 |
| WO | 2009/081325 | 7/2019 |

OTHER PUBLICATIONS

Sencan, et al., "Speclial Demultiplexing in Holographic and Fluorescent On-chip Microscopy" Scientific Reports 4 (1), 1-9, 2014.

Liang et al., "The Copper(I)-Catalyzed Alkyne-Azide Cycloaddition (CuAAC) 'Click' Reaction and its Applications. An Overview," Coordination Chemistry Review, 225:2933-2945 (2011).

Yang et al., "Poly(thymine)-templated Selective Formation of Copper Nanoparticles for Alkaline Phosphatase Analysis Aided by Akyne-Azide Cycloaddition 'Click' Reaction," Applied Nano Materials, 1:168-174 (2017).

* cited by examiner

TWO-FILTER LIGHT DETECTION DEVICES AND METHODS RELATED TO SAME

CROSS-REFERENCE TO RELATED APPLICATIONS

This patent application is a continuation of U.S. patent application Ser. No. 16/208,949, filed Dec. 4, 2018 and entitled Two-Filter Light Detection Devices and Methods Related to Same, which claims priority to U.S. Provisional Patent Application No. 62/609,903, filed Dec. 22, 2017, and entitled Two-Filter Light Detection Devices and Methods of Manufacturing Same, and Dutch Application No. 2020625, filed on Mar. 20, 2018, and entitled Two-Filter Light Detection Devices and Methods of Manufacturing Same. The entire contents of each of the aforementioned applications are hereby incorporated herein by reference.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some conventional fluorescent-detection protocols, an optical system is used to direct an excitation light onto fluorescently-labeled analytes and to also detect the fluorescent signals that may emit from the analytes. However, such optical systems can be relatively expensive and involve a relatively large benchtop footprint. For example, such optical systems may include an arrangement of lenses, filters, and light sources.

In other proposed detection systems, the controlled reactions occur on local support surfaces or within predefined reaction chambers provided over an electronic solid-state light detector or imager (e.g., a complementary metal-oxide-semiconductor (CMOS) detector or a charged-coupled device (CCD) detector) that does not involve a large optical assembly to detect the fluorescent emissions. However, such proposed solid-state imaging systems may have some limitations. For example, fluidically delivering reagents (e.g., fluorescently-labeled molecules) to the analytes that are located on the electronic device of such systems may present challenges. In some scenarios, the reagent solution may breach the electronic device and corrode components thereof, for example.

BRIEF DESCRIPTION

In one aspect of the present disclosure, a device is provided. The device comprises a reaction structure to contain a reaction solution and a plurality of reaction sites that generate light emissions in response to incident excitation light after treatment with the reaction solution. The reaction solution may initiate a reaction and/or form a reaction product at the reaction sites that generate the light emissions in response to the excitation light. The reaction structure is positioned over a device base of the device. The device also comprises a plurality of light sensors within the device base, and device circuitry within the device base electrically coupled to the plurality of light sensors and configured to transmit data signals based on photons detected by the light sensors. The device further comprises a plurality of light guides with input regions to receive the excitation light and the light emissions from at least one corresponding reaction site, the light guides extending into the device base from the input regions toward at least one corresponding light sensor. Each of the plurality of light guides comprises a first filter region formed of a first filter material to filter the excitation light of at least a first wavelength and permit the light emissions of a second wavelength to pass therethrough to the at least one corresponding light sensor, and a second filter region formed of a second filter material to filter the excitation light of at least the first wavelength and permit the light emissions of a third wavelength to pass therethrough to the at least one corresponding light sensor.

In some examples, at least one first reaction site of the plurality of reaction sites emits light of at least the second and third wavelengths in response to excitation light of the first wavelength after treatment with the reaction solution (e.g., after the reaction solution has initiated reactions and/or formed at least one reaction product at the reaction sites). In some examples, at least one first reaction site of the plurality of reaction sites emits light of at least the second and third wavelengths in response to excitation light of the first wavelength and a fourth wavelength, respectively, after treatment with the reaction solution. In some examples, at least one first reaction site of the plurality of reaction sites emits light emissions of the second wavelength in response to excitation light of the first wavelength after treatment with the reaction solution, and at least one second reaction site of the plurality of reaction sites emits light emissions of the third wavelength in in response to excitation light of a fourth wavelength after treatment with the reaction solution.

In some examples, the device further comprises a support layer within a bottom portion of the light guides extending below and about a bottom portion of the first filter regions. In some such examples, the support layer is comprised of an oxide, a nitride, or a combination thereof. In other such examples, the second region of the light guides extends over the support layer and about the first filter regions. In some such examples, the first and second regions of the light guides form the input regions of the light guides.

In some examples, the device further comprises a second liner layer that is positioned between the support layer and the device circuitry at the bottom portion of the light guides, and that is positioned between the second filter region and the device circuitry within a top portion of the light guides. In some such examples, the second liner layer comprised a silicon nitride shield layer. In some examples, the device circuitry of the device base forms complementary metal-oxide semiconductor (CMOS) circuits.

In some examples, the first filter material further filters the light emissions of the third wavelength, and the second filter material further filters the light emissions of the second wavelength. In some examples, the first filter material is a polymer material with a first dye, and the second filter material is a polymer material with a second dye that differs from the first dye. In some examples, each of the plurality of reaction sites are immobilized to the reaction structure within at least one reaction recess of the reaction structure.

In some examples, the reaction solution initiates a reaction and/or forms a reaction product at the reaction sites that generates the light emissions of the second and third wavelengths in response to the incident excitation light. In some such examples, the at least one reaction site comprises at least one analyte, and the reaction solution comprises an aqueous solution containing at least one fluorescently-labeled molecule. In some such examples, the at least one analyte comprises an oligonucleotide, and the at least one fluorescently-labeled molecule comprises a fluorescently-labeled nucleotide.

In another aspect of the present disclosure, a biosensor is provided. The biosensor comprises any of the devices described above. The biosensor also comprises a flow cell mounted to the device, and the reaction sites contained on the reaction structure. The flow cell comprises the reaction solution and at least one flow channel that is in fluid communication with the reaction sites of the reaction structure to direct the reaction solution thereto.

In another aspect of the present disclosure, a method is provided. The method comprises forming a plurality of trenches within a device base comprising a plurality of light sensors and device circuitry electrically coupled to the light sensors configured to transmit data signals based on photons detected by the light sensors. The plurality of trenches each extend from a top surface of the device base and toward at least one corresponding light sensor. The method also comprises depositing a support layer over inner surfaces of the plurality of trenches. The method further comprises filling the plurality of trenches over the deposited support layer with a first filter material that filters light of at least a first wavelength and permits light of a second wavelength to pass therethrough to the at least one corresponding light sensor. The method also comprises removing an upper portion of the deposited support layer within the plurality of trenches positioned between the device base and the first filter material to form a plurality of voids. The method further comprises filling the plurality of voids with a second filter material that filters light of at least the first wavelength and permits light of a third wavelength to pass therethrough to the at least one corresponding light sensor to form a plurality of light guides. The method also comprises forming a reaction structure over the device base and the plurality of light guides for containing a reaction solution and at least one reaction site that generates light of at least one of the second and third wavelengths after treatment with the reaction solution in response to incident excitation light of at least the first wavelength.

In some examples, at least one first reaction site emits light of at least the second and third wavelengths in response to excitation light of the first wavelength after treatment with the reaction solution (e.g., after the reaction solution has initiated reactions and/or formed at least one reaction product at the reaction sites). In some examples, at least one first reaction site emits light of at least the second and third wavelengths in response to excitation light of the first wavelength and a fourth wavelength, respectively, after treatment with the reaction solution. In some examples, at least one first reaction site emits light emissions of the second wavelength in response to excitation light of the first wavelength after treatment with the reaction solution, and at least one second reaction site emits light emissions of the third wavelength in in response to excitation light of a fourth wavelength after treatment with the reaction solution.

In some examples, removing the upper portion of the deposited support layer within the plurality of trenches forms a support layer portion that extends below and about a bottom portion of the first filter material. In some examples, the method further comprises depositing a second liner layer over the inner surfaces of the plurality of trenches and over the top surface of the device base prior to depositing the support layer such that the support layer extends over the second liner layer. In some examples, the first filter material further filters the light of the second wavelength, and the second filter material further filters the light of the first wavelength. In some examples, the first filter material comprises a polymer material with a first dye, and the second filter material comprises a polymer material with a second dye that differs from the first dye.

It should be appreciated that all combinations of the foregoing aspects and additional concepts discussed in greater detail below (provided such concepts are not mutually inconsistent) are contemplated as being part of the inventive subject matter disclosed herein.

These and other objects, features and advantages of this disclosure will become apparent from the following detailed description of the various aspects of the disclosure taken in conjunction with the accompanying drawings.

DRAWINGS

These and other features, aspects, and advantages of the present invention will become better understood when the following detailed description is read with reference to the accompanying drawings, which are not necessarily drawn to scale and in which like reference numerals represent like aspects throughout the drawings, wherein.

DETAILED DESCRIPTION

Figure 1:
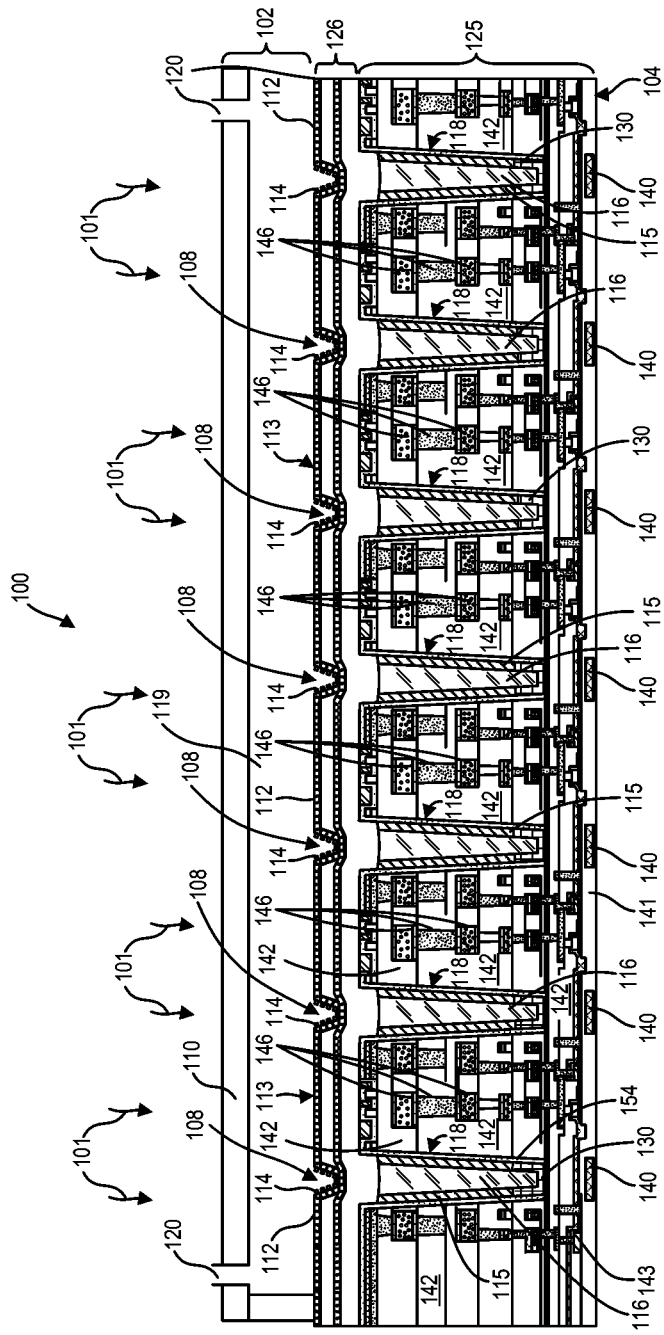
FIG. 1 illustrates, in one example, a cross-section of a biosensor in accordance with the present disclosure.

Aspects of the present disclosure and certain examples, features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the relevant details. It should be understood, however, that the detailed description and the specific examples, while indicating aspects of the disclosure, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout disclosure, may be applied to modify any quantitative representation that could permissibly vary without resulting in a change in the basic function to which it is related. Accordingly, a value modified by a term or terms, such as "about" or "substantially," is not limited to the precise value specified. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. In some instances, the approximating language may correspond to the precision of an instrument for measuring the value.

Terminology used herein is for the purpose of describing particular examples only and is not intended to be limiting. As used herein, the singular forms "a", "an" and "the" are intended to include the plural forms as well, unless the context clearly indicates otherwise. Furthermore, references to "one example" are not intended to be interpreted as excluding the existence of additional examples that also incorporate the recited features. Moreover, unless explicitly stated to the contrary, the terms "comprising" (and any form of "comprise," such as "comprises" and "comprising"), "have" (and any form of "have," such as "has" and "having"), "include" (and any form of "include," such as "includes" and "including"), and "contain" (and any form of "contain," such as "contains" and "containing") are used as open-ended linking verbs. As a result, any examples that "comprises," "has," "includes" or "contains" one or more step or element possesses such one or more step or element, but is not limited to possessing only such one or more step or element. As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channels that deliver reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially basic/alkaline, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7. In some examples, the reaction sites are provided or spaced apart in a predetermined manner, such as in a uniform or repeating pattern. In some other examples, the reaction sites are randomly distributed. Each of the reaction sites may be associated with one or more light guides and light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, the designated reaction is a positive binding event, such as incorporation of a fluorescently labeled biomolecule with an analyte-of-interest, for example. More generally, a designated reaction may be a chemical transformation, chemical change, or chemical interaction. The designated reaction may also be a change in electrical properties. In particular examples, the designated reaction includes the incorporation of a fluorescently-labeled molecule to at least one analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In alternative examples, the detected light emissions or signals is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction solution," "reaction component" or "reactant" includes any substance that may be used to obtain at least one designated reaction. For example, reaction components include reagents, enzymes, samples, other biomolecules, and buffer solutions. The reaction components may be delivered to a reaction site in a solution and/or immobilized at a reaction site. The reaction components may interact directly or indirectly with another substance, such as the analyte-of-interest immobilized at a reaction site. In some examples, the reaction solution may be relatively highly acidic (e.g., a pH of less than or equal to about 5) or relatively highly alkaline/basic (e.g., a pH of greater than or equal to about 8).

As used herein, the term "reaction site" is a localized region where at least one designated reaction may occur. A reaction site may include support surfaces of a reaction structure or substrate where a substance may be immobilized thereon. For example, a particular reaction site may include a substantially planar surface of a reaction structure (which may be positioned in a channel of a flow cell) that has a colony of nucleic acids thereon. In some examples, the nucleic acids in the colony have the same sequence, being for example, clonal copies of a single stranded or double stranded template. However, in some examples a reaction site may contain only a single nucleic acid molecule, for example, in a single stranded or double stranded form. Furthermore, a plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" includes a defined spatial region of the support structure (which is often in fluid communication with a flow channel). The reaction recesses may be at least partially separated from the surrounding environment or other spatial regions. For example, a plurality of reaction recesses may be separated from each other by shared walls. As a more specific example, the reaction recesses may be nanowells that include an indent, pit, well, groove, or open-sided cavity or depression defined by interior surfaces and defining an opening or aperture so that the nanowells are in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., a CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

FIGS. 1-8 illustrate a cross-section of a portion of a biosensor 100 formed in accordance with one example. As shown, the biosensor 100 may include a flow cell 102 that is coupled directly or indirectly to a light detection device 104. The flow cell 102 may be mounted to the light detection device 104. In the illustrated example, the flow cell 102 is affixed directly to the light detection device 104 through one or more securing mechanisms (e.g., adhesive, bond, fasteners, and the like). In some examples, the flow cell 102 may be removably coupled to the light detection device 104.

The biosensor 100 and/or detection device 104 may be configured for biological or chemical analysis to obtain any information or data that relates thereto. In particular examples, the biosensor 100 and/or detection device 104 may comprise a nucleic acid sequencing system (or sequencer) configured for various applications, including but not limited to de novo sequencing, resequencing of whole genomes or target genomic regions, and metagenomics. The sequencing system may be configured to perform DNA or RNA analysis. In some examples, the biosensor 100 and/or detection device 104 is configured to perform a large number of parallel reactions within the biosensor 100 and/or detection device 104 to obtain information relating thereto.

The flow cell 102 may include one or more flow channels that direct a solution to or toward reaction sites 114 on the detection device 104, as explained further below. The flow cell 102 and/or biosensor 100 may thereby include, or be in fluid communication with, a fluid storage system (not shown) that may store various reaction components or reactants that are used to conduct the designated reactions therein, for example. The fluid storage system may also store fluids for washing or cleaning a fluid network and the biosensor 100 and/or detection device 104, and potentially for diluting the reactants. For example, the fluid storage system may include various reservoirs to store samples, reagents, enzymes, other biomolecules, buffer solutions, aqueous, oil and other non-polar solutions, and the like. As noted above, the fluid or solution provided on the reaction structure 126 may be relatively acidic (e.g., pH less than or equal to about 5) or basic/alkaline (e.g., pH greater than or equal to about 8). Furthermore, the fluid storage system may also include waste reservoirs for receiving waste products from the biosensor 100 and/or detection device 104.

Figure 3:
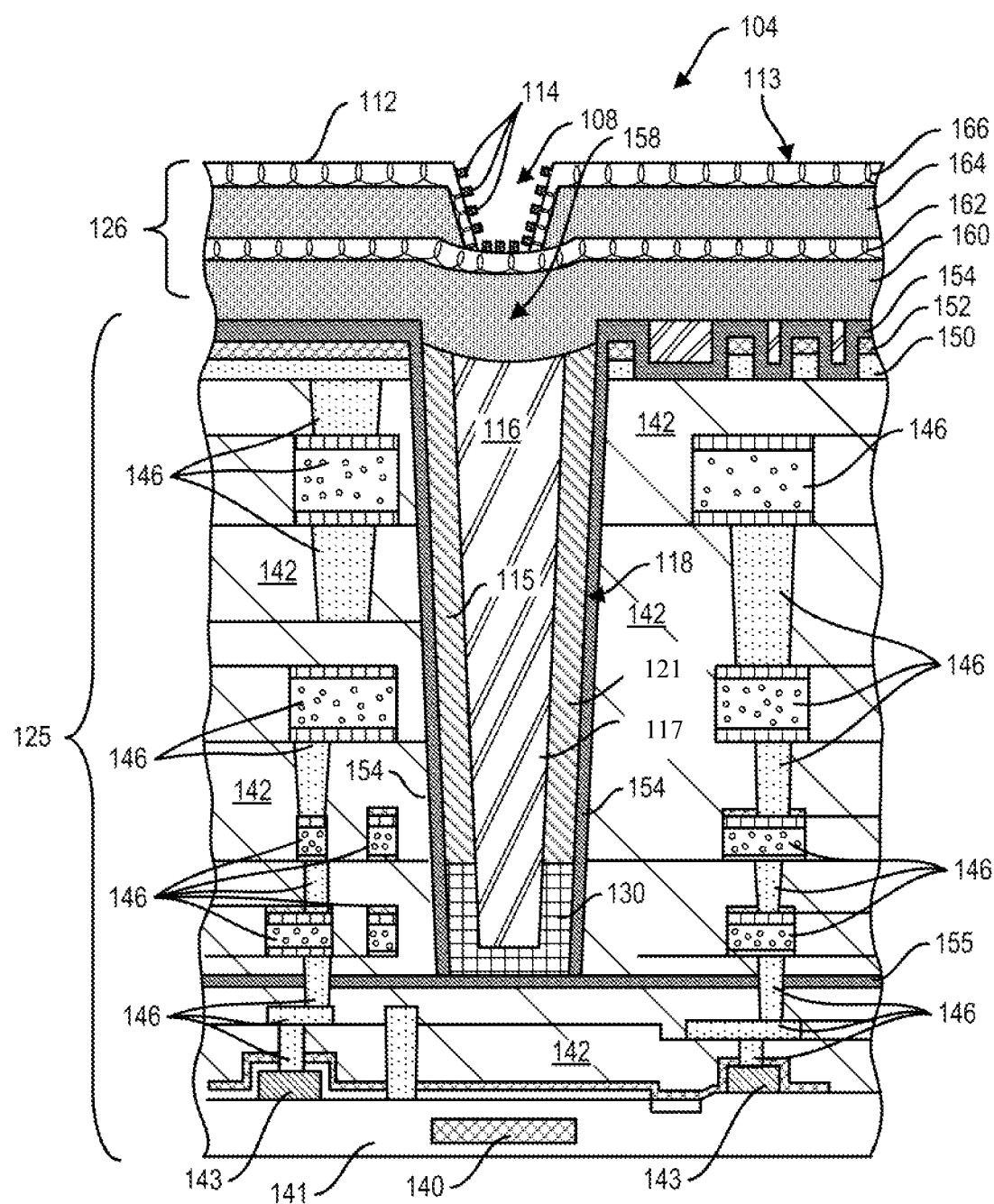
FIG. 3 illustrates, in one example, a side cross-sectional view of a portion of the biosensor of FIG. 1 illustrating a portion of a reaction structure and a light guide thereof.

In the illustrated example, the light detection device 104 includes a device base 125 and a reaction structure 126 overlying the device base 125, as shown in FIGS. 1 and 3-8. In particular examples, the device base 125 includes a plurality of stacked layers (e.g., silicon layer or wafer, dielectric layer, metal-dielectric layers, etc.). The device base 125 may include a sensor array 124 of light sensors 140, and a guide array of light guides 118, as shown in FIG. 3. As shown in FIGS. 1 and 3-8, the reaction structure 126 may include an array of reaction recesses 108 that have at least one corresponding reaction site 114 provided therein (e.g., immobilized on a surface thereof). In certain examples, the light detection device 104 is configured such that each light sensor 140 corresponds (and potentially aligns) with a single light guide 118 and/or a single reaction recess 108 such that it receives photons only therefrom. However, in other examples, a single light sensor 140 may receive photons through more than one light guide 118 and/or more than one reaction recess 108. Similarly, a single light sensor 140 may receive photons from reaction site 114 or from multiple reaction sites 114. A single light sensor 140 may thereby form one pixel or more than one pixel.

Figure 2:
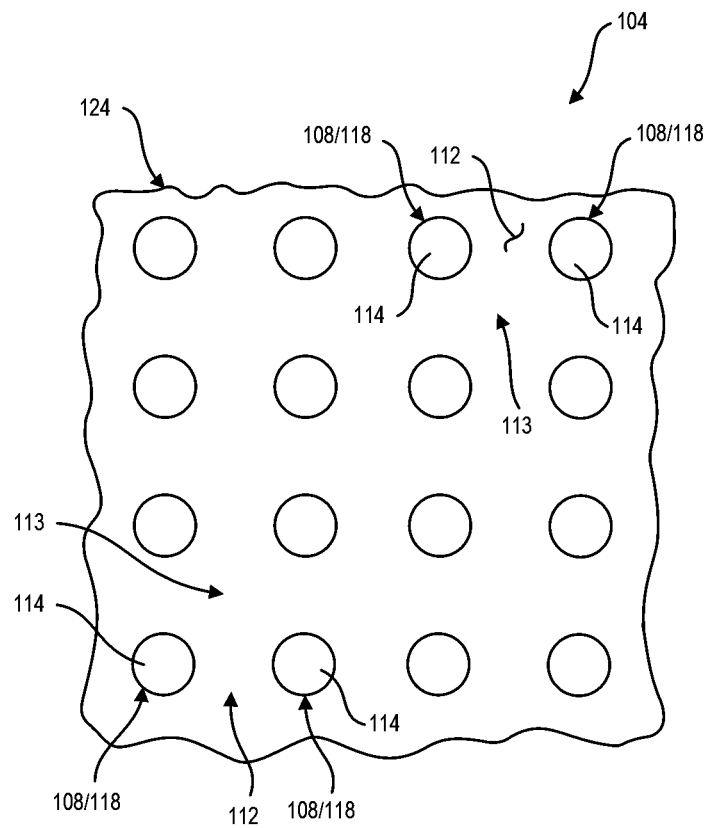
FIG. 2 illustrates, in one example, a top view of a device base of the biosensor of FIG. 1.

As shown in FIG. 2, the array of reaction recesses 108 and/or light guides 118 (and potentially light sensors 140) may be provided in a defined repeating pattern such that at least some of the recesses 108 and/or light guides 118 (and potentially light sensors 140) are equally spaced from one another in a defined positional pattern. In other examples, the reaction recesses 108 and/or light guides 118 (and potentially light sensors 140) may be provided in a random pattern, and/or at least some of the reaction recesses 108 and/or light guides 118 (and potentially light sensors 140) may be variably spaced from each other.

As shown in FIGS. 1 and 2, the reaction structure 126 of the detection device 104 may define a detector surface 112 over which a reaction solution may flow and reside, as explained further below. The detector surface 112 of the reaction structure 126 may be the top exposed surface of the detection device 104. The detector surface 112 may comprise the surfaces of the recesses 108 and interstitial areas 113 extending between and about the recesses 108.

Figure 4:
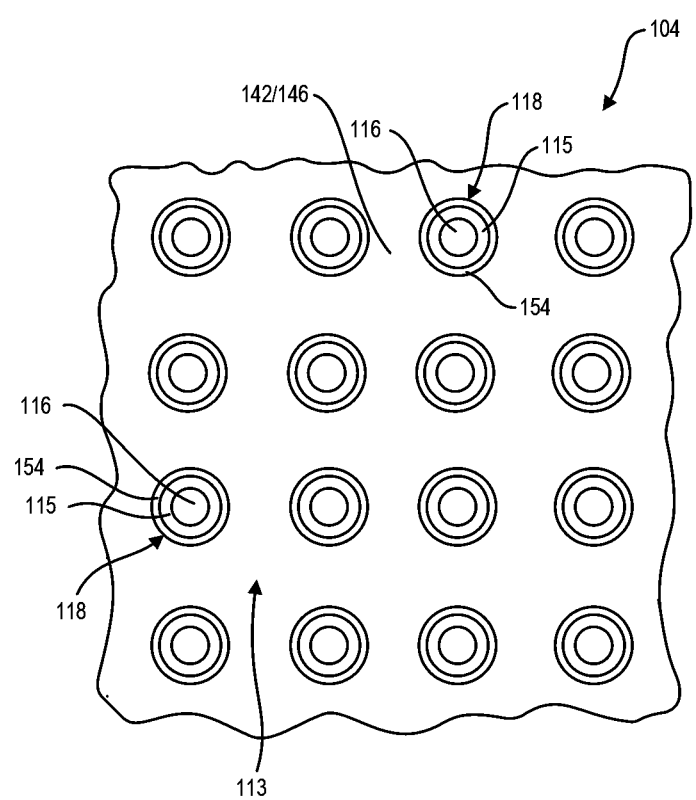
FIG. 4 illustrates, in one example, a top cross-sectional view of a portion of the biosensor of FIG. 1 illustrating an array of light guides.

The detector surface 112 of the light detection device 104 may be functionalized (e.g., chemically or physically modified in a suitable manner for conducting designated reactions). For example, the detector surface 112 may be functionalized and may include a plurality of reaction sites 114 having one or more biomolecules immobilized thereto, as shown in FIGS. 1, 3 and 4. As noted above, the detector surface 112 may include an array of reaction recesses 108 (e.g., open-sided reaction chambers). Each of the reaction recesses 108 may include one or more of the reaction site 114. The reaction recesses 108 may be defined by, for example, a change in depth (or thickness) along the detector surface 112. In other examples, the detector surface 112 may be substantially planar.

As shown in FIGS. 3 and 4, the reaction sites 114 may be distributed in a pattern along the detector surface 112, such as within the reaction recesses 108. For instance, the reaction sites 114 may be located in rows and columns along the reaction recesses 108 in a manner that is similar to a microarray. However, it is understood that various patterns of reaction sites 114 may be used. The reaction sites 114 may include biological or chemical substances that emit light signals, as explained further below. For example, the biological or chemical substances of the reactions sites 114 may generate light emissions in response to the excitation light 101. In particular examples, the reaction sites 114 include clusters or colonies of biomolecules (e.g., oligonucleotides) that are immobilized on the detector surface 112 within the reaction recesses 108.

As shown in FIG. 1, in one example the flow cell 102 includes at least one sidewall and a flow cover 110. The least one sidewall may be coupled to the detector surface 112 and extend between the flow cover 110 and the detector surface 112. The flow cell 102 may be configured so that a flow channel 119 is formed between the flow cover 110 and the detector surface 112 of the light detection device 104. In some examples, the flow channel 119 may include a height (extending between the flow cover 110 and the detector surface 112) within the range of about 50 to about 400 μm (microns), or about 80 to about 200 μm, for example. In one example, the height of the flow channel 119 is about 100 μm. The flow cover 110 may comprise a material that is transparent to the excitation light 101 (e.g., a plastic, class, or polymer material) propagating from an exterior of the biosensor 100 and toward/into the flow channel 119, as shown in FIG. 1. It is noted that excitation light 101 may approach the flow cover 110 from any angle, and along the same or different angles.

The excitation light 101 may be emitted or produced from any illumination system or source (not shown), which may or may not be part of the bioassay system, biosensor 100 or light detection device 104. In some examples, the illumination system may include a light source (e.g., one or more LED) and, potentially, a plurality of optical components to illuminate at least the reaction structure 126 of the detection device 104. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In a particular example, the illumination system is configured to direct the excitation light 101 to reaction sites 114 within the recesses 108 of the reaction structure 126 of the detection device 104. In some examples, the illumination system may emit the excitation light 101 of a certain wavelength or within a range of wavelengths, such as a wavelength within the range of about 300 nm to about 700 nm, or within the range of about 400 nm to about 600 nm. In some examples, the illumination system may emit the excitation light 101 at a certain wavelength or wavelengths that excites the biological or chemical substance(s) of the reaction sites 114 to emit light emissions of a differing wavelength or wavelengths. For example, in one example where the device includes reaction sites 114 within a single reaction recess 108 or differing reaction recesses 108 that include first and second fluorophores that are excited by blue wavelengths of light, the excitation light of may be about 400 nm, the light emissions from the reaction sites 114 with the first fluorophore may be about 500 nm (or within the range of about 450 nm to about 550 nm), and light emissions from the reaction sites 114 with the second fluorophore may be about 650 nm (or within the range of about 600 nm to about 550 nm).

In some other examples, the illumination system may emit excitation light 101 at differing wavelengths ranges of wavelengths (that do not overlap) that independently or selectively excite differing biological or chemical substance(s) of differing reaction sites 114 to emit light emissions of differing wavelengths or ranges of wavelengths. For example, in one example where the device includes reaction sites 114 within a single reaction recess 108 or differing reaction recesses 108 that include first and second fluorophores that are excited by differing wavelengths or ranges of wavelengths of light, the lighting system may emit a first excitation light 101 of a first wavelength or range of wavelengths (e.g., a blue excitation light (of about 400 nm for example) or a green excitation light (about 530 nm for example)) that cause the reaction sites 114 with the first fluorophore to emit light of a first wavelength or range of wavelengths (e.g., within the range of about 450 nm to about 550 nm, or within the range of about 600 nm to about 550 nm), and emit a second excitation light 101 of a first wavelength or range of wavelengths (e.g., a blue excitation light (of about 400 nm for example) or a green excitation light (about 530 nm for example)) at the same time period or during a differing time period (i.e., during a single light detection event or during differing light detection events) than the first excitation light 101 that cause the reaction sites 114 with the second fluorophore to emit light of a second wavelength or range of wavelengths (e.g., within the range of about 450 nm to about 550 nm, or within the range of about 600 nm to about 550 nm).

As also shown in FIG. 1, the flow cover 110 may include at least one port 120 that is configured to fluidically engage the flow channel 119 and, potentially, other ports (not shown). For example, the other ports may be from a cartridge or a workstation that comprised the reaction solution or another biological or chemical substance. The flow channel 119 may be configured (e.g., sized and shaped) to direct a fluid or solution, such as the reaction solution, along the detector surface 112.

FIGS. 3 and 4 show the example of the detection device 104 in greater detail than FIG. 1. More specifically, FIGS. 3 and 4 show a single light sensor 140, a single light guide 118 for directing and passing light emissions from at least one reaction site 114 associated therewith toward the light sensor 140, and associated circuitry 146 for transmitting signals based on the light emissions (e.g., photons) detected by the light sensor 140. It is understood that the other light sensors 140 of the sensor array 124 (FIGS. 1 and 2) and associated components may be configured in an identical or similar manner. It is also understood, however, the light detection device 104 is not required to be manufactured uniformly throughout. Instead, one or more light sensors 140 and/or associated components may be manufactured differently or have different relationships with respect to one another.

The circuitry 146 may include interconnected conductive elements (e.g., conductors, traces, vias, interconnects, etc.) that are capable of conducting electrical current, such as the transmission of data signals that are based on detected photons. For example, in some examples, the circuitry 146 may comprise a microcircuit arrangement. The light detection device 104 and/or the device base 125 may comprise at least one integrated circuit having an array of the light sensors 140. The circuitry 146 positioned within the detection device 104 may be configured for at least one of signal amplification, digitization, storage, and processing. The circuitry 146 may collect (and potentially analyze) the detected light emissions and generate data signals for communicating detection data to a bioassay system. The circuitry 146 may also perform additional analog and/or digital signal processing in the light detection device 104.

The device base 125 and the circuitry 146 may be manufactured using integrated circuit manufacturing processes, such as processes used to manufacture charged-coupled devices or circuits (CCD) or complementary-metal-oxide semiconductor (CMOS) devices or circuits. For example, as shown in FIG. 3, the device base 125 may be a CMOS device comprising of a plurality of stacked layers including a sensor base 141, which may be a silicon layer (e.g., a wafer) in some examples. The sensor base 141 may include the light sensor 140, and gates 143 formed thereon. The gates 143 may be electrically coupled to the light sensor 140. When the light detection device 104 is configured as shown in FIG. 3, the light sensor 140 may be electrically coupled to the circuitry 146 through the gates 143, for example.

At least some of the circuitry 146 may be provided within device substrate layers of the device base 125 of the detection device 104, through/into which the lights guides 118 may each extend. In some examples, each of the substrate layers may include interconnected conductive elements that forms at least part of the device circuitry 146, and dielectric material 142 adjacent to (and potentially surrounding) the conductive elements of the circuitry 146, as shown in FIG. 3. The conductive elements of the circuitry 146 may be embedded within the dielectric material 142. As also shown in FIG. 3, the lights guides 118 may extend through the dielectric material 142 and may be spaced from the circuitry 146. Various metallic elements and/or dielectric materials may be used, such as those suitable for integrated circuit manufacturing (CMOS manufacturing). For example, in some examples, the conductive elements/circuitry 146 may be metallic elements, such as W (tungsten) elements, Cu (copper) elements, Al (aluminum) elements, or a combination thereof (but it is understood that other materials and configurations may be used). In some examples, the dielectric material may be SiO2 (but it is understood that other materials and configurations may be used).

As used herein, the term "layer" is not limited to a single continuous body of material unless otherwise noted. For example, the sensor layer 141 and/or the device layers of the device base 125 may include multiple sub-layers that are different materials and/or may include coatings, adhesives, and the like. Furthermore, one or more of the layers (or sub-layers) may be modified (e.g., etched, deposited with material, etc.) to provide the features described herein.

As shown in FIGS. 3 and 4, the reaction structure 126 may comprise of one or more layers that form the reaction recesses 104 extending therein. The reaction structure 126 may extend along a top outer surface of the device base 125. In the illustrated example, the reaction structure 126 is deposited directly along the top or outer surface of a first liner layer 154 and the first and second filter material 116, 115 of the device base 125, as described further below. However, an intervening layer may be disposed between the reaction structure 126 and the device base 125 in other examples. The reaction structure 126 may include one or more materials that are configured to allow the excitation light signals 101 and emitted light signals from the reaction sites 114 (after treatment with the reaction solution) within the recesses 108 to pass therethrough and into an opening 158 of one or more light guide 118 corresponding to a particular reaction recess 108. In some examples, the reaction structure 126 may include one more layer or other feature that prevents crosstalk or "sharing" of emitted light from a particular reaction site 114/reaction recesses 108 from to a non-corresponding sensor 140.

The reaction structure 126 may comprise a plurality of differing layers, as shown in FIGS. 3 and 4. In the illustrated example, the reaction structure 126 may include a first reaction layer 160 that extends over (directly or indirectly) device base 125 (e.g., over the first liner layer 154) and the opening 158 of the light guides 118 (e.g., the first and second filter material 116, 115) of the device base 125, as shown in FIGS. 3 and 4. As also shown in FIGS. 3 and 4, in the illustrated example, the reaction structure 126 further includes a second layer 162 that extends over (directly or indirectly) the first layer 160. The reaction structure 126 of illustrated example also includes a third layer 164 that extends over (directly or indirectly) the second layer 162, and a fourth layer 166 that extends over (directly or indirectly) the third layer 164. The reaction recesses 108 may extend at least into the third layer 164.

The fourth layer 166 may form the inner surfaces (e.g., side walls and a bottom wall) of the reaction recesses 108 by extending over an indentation (e.g., a cavity or a void) in the third layer 164, as shown in FIGS. 3 and 4. The fourth layer 166, and potentially the second layer 162, may form the detector surface 112, as shown in FIGS. 3 and 4. In some cases, the fourth layer 166, and potentially the second layer 162, may be configured to provide a solid surface that permits chemicals, biomolecules or other analytes-of-interest to be immobilized thereon. For example, each of the reaction sites 114 may include a cluster of biomolecules that are immobilized to the detector surface 112, which may comprise the fourth layer 166, and potentially the second layer 162. Thus, the fourth layer 166, and potentially the second layer 162, may comprise a material that permits the reaction sites 114 to be immobilized thereto. The first layer 160 and the fourth layer 166 (and potentially the second layer 162 and the third layer 164) may comprise a material that is at least substantially transparent to the excitation light 101 and the emission light of the reaction sites 114. In addition, the fourth layer 166, and potentially the second layer 162, may be physically or chemically modified to facilitate immobilizing the biomolecules and/or to facilitate detection of the light emissions.

By way of example and as shown in the illustrated example of FIGS. 3 and 4, the first layer 160 and the third layer 164 may comprise a first material, and the second layer 162 and the fourth layer 166 may comprise a second material that differs from the first material. In some such examples, the first material is SiN, and the second material is TaO.

However, the reaction structure 126 may comprise differing layers (e.g., different layers, fewer layers, and/or additional layers) and/or differing materials.

As shown in FIGS. 3 and 4, the device base 125 of the detection device 104 may include a first shield layer 150 that extends over (directly or indirectly) the stacked layers (e.g., metal-dielectric layers) of the device base 125, such as over the dielectric material 142 and the conductive circuitry components 146. The first shield layer 150 may include a material that is configured to block, reflect, and/or significantly attenuate the excitation light 101 and/or the light emissions from the reaction sites 114 (e.g., light signals that are propagating from the flow channel 118). By way of example only, the first shield layer 150 may comprise tungsten (W).

The first shield layer 150 may include at least one an aperture therethrough which aligns, at least partially, with at least one corresponding light guide 118. The first shield layer 150 may include an array of such apertures. In some examples, the first shield layer 150 may extend entirely about the apertures therein. As such, the light signals from excitation light 101 and/or the light emissions from the reaction sites 114 may be blocked, reflected, and/or significantly attenuated to prevent the light signals from passing through the device base 125 outside of the light guides 118 and being detected by the light sensors 140. In some examples, the first shield layer 150 extends continuously between adjacent apertures or light guides 118 and/or openings extending thereto. In some other examples, the first shield layer 150 does not extend continuously between adjacent apertures or light guides 118 such that one or more other aperture exists in the first shield layer 150, which may allow the excitation light 101 and/or the light emissions from the reaction sites 114 to pass therethrough.

In some examples, the device base 125 of the detection device 104 may include a second shield layer 152 that extends over (directly or indirectly) the first shield layer 150, as shown in FIGS. 3 and 4. The second shield layer 152 may include anti-reflective material and/or a material that prevents contamination of the underlying portions of the device base 125. By way of example only, the second shield layer 152 may comprise SiON. In some examples, the second shield layer 152 may be configured to prevent contaminated, such as sodium, from interacting with the first shield layer 150, the dielectric material 142 and/or the conductive (e.g., metal) components of the device circuitry 146. In some examples, the second shield layer 152 may mimic the configuration of the first shield layer 150. For example, the second shield layer 152 may include at least one aperture therethrough which aligns, at least partially, with at least one light guide 118, as shown in FIGS. 3 and 4. The second shield layer 152 may include an array of such apertures. In some examples, the second shield layer 152 may extend about the apertures therein. In some examples, the second shield layer 152 extends continuously between adjacent light guides 118 and/or openings extending thereto. In some other examples, the second shield layer 152 does not extend continuously between adjacent light guides 118 and/or openings extending thereto such that one or more other aperture exists in the second shield layer 152, as shown in FIGS. 3 and 4.

In some examples, the light detection device 104 may include a first liner layer 154 that extends over the device base 125 and about the light guides 118, as shown in FIGS. 3 and 4. The first liner layer 154 may be a continuous conformal layer formed on the device base 125. The first liner layer 154 may be void of defined apertures. However, the first liner layer 154 may include internal discontinuities, pores, breaks or the like that allow a liquid or solution, such as the reaction solution, to flow therethrough, as explained further below. The first liner layer 154 may be chemically reactive with respect to the reaction solution. For example, due to the composition (e.g., water and/or oil) and/or relatively high acidity (e.g., a pH equal to or less than about 5) or relatively high basicity (e.g., a pH equal to or greater than about 8) of the reaction solution, the reaction solution may chemically react with the material of the first liner layer 154 when exposed thereto and cause the material to be dissolved or otherwise detached (i.e., etch the liner layer 154). Over an exposure time, the reaction solution may thereby etch through the first liner layer 154 and, ultimately, interact with and corrode or otherwise interfere with the functioning of the device circuitry 146. For example, the first liner layer 154 may be a silicon nitride layer (or otherwise include SiN), and the relatively high acidic or basic reaction solution may etch the SiN when exposed thereto.

In the illustrated examples, the first liner layer 154 extends between the reaction structure 126 and the second shield layer 152 on the top upper portion of the device base 125 (and/or any layer on the top or upper portion of the device base 125) in the interstitial regions 113, and extends along the light guides 118, as shown in FIGS. 3 and 4. In the illustrated example, the first liner layer 154 extends about the light guides 118 and adjacent the dielectric material 142 of the device base 125, as shown in FIGS. 3 and 4. As also shown in FIGS. 3 and 4, the first liner layer 154 may extend about the light guides 118 such that it is positioned between (e.g., directly between) the dielectric material 142 of the device base 125 and the support liner 130 and second filter region 121 of the light guides 118. The first liner layer 154 may be configured as an anti-reflective layer or a reflective layer (e.g., to ensure the light emitted from the reaction sites 114 passes through the light guides 118), a contamination prevention layer (e.g., to prevent sodium contamination into the device base 125) and/or an adhesion layer (e.g., to adhere the support liner 130 and second filter region 121 of the light guides 118 to the dielectric material 142). In some examples, the liner layer 154 may be configured as a contamination prevention layer that prevents any ionic species from penetrating into device layers (e.g., metal-dielectric layers). In some examples, the liner layer 154 comprises SiN. In some examples, the liner layer 154 comprises a SiN layer.

As shown in FIGS. 3 and 4, the first liner layer 154 may be of a substantially uniform thickness. In other examples, the thickness of the first liner layer 154 may vary. For example, the portions of the first liner layer 154 extending over the top portion of the device base 125 may be a first thickness, and the portions of the first liner layer 154 extending about the light guides 118 may be a second thickness that is thicker or thinner than the first thickness. As another example, the thickness of the portions of the first liner layer 154 extending about the light guides 118 may be vary along the depth of the within the device base 125 (e.g., may taper with depth into the device base 125). In some examples, the thickness of the first liner layer 154 may be within the range of about 10 nm to about 100 nm. In the illustrated example, the first liner layer 154 is about 50 nm thick.

As shown in FIG. 3, the device base 125 may also include a second liner layer 155 positioned within the device layers and beneath the light guides 118. The second liner layer 155 may be substantially similar or the same as the first liner layer 154 but for its position within the device base 125. In some examples, the second liner layer 155 may extend immediately below the support liner 130 along the bottom of the light guides 118, as shown in FIG. 3. In this way, the first liner layer 154 and the second liner layer 155 may extend entirely about the light guides 118 but for the openings 158 of the light guides 118 beneath the reaction recesses 108.

As discussed above, the device base 125 of the detection device 104 may include the support liner or layer 130 positioned at a bottom portion of the light guides 118, as shown in FIG. 3. The support liner 130 may extend (directly or indirectly) between the first filter region 117 and the dielectric material 142, and between the first filter region 117 and the second liner layer 155. For example, the support liner 130 may extend about the first filter region 117 and between (directly or indirectly) the first filter region 117 and the first liner layer 154, as shown in FIG. 3. In this way, the support liner 130 may extend about a bottom portion of the first filter region 117, including about the side and bottom surfaces thereof. The support liner 130 may extend fully about the first filter material 116 of the light guides 118. As shown in FIG. 3, the second filter region 121 may extend above the support liner 130 in an upper portion of the light guides 118. The support liner 130 may thereby support or extend below the second filter region 121. In some examples, the support liner 130 may extend immediately below the second filter region 121. The support liner 130 and the second filter region 121 may thereby combine to form a layer that extends about the first filter material 116 and is positioned between the first filter material 116 and the first liner layer 154 and/or dielectric material 142 of the device base 125, as shown in FIG. 3.

The thickness of the support liner 130 may be any thickness. In some examples, the thickness of the support liner 130 may be within the range of about 100 nm and about 1 micron, or within the range of about 100 nm and about 500 nm. In some examples, the thickness of the support liner 130 may be the same or substantially similar thickness to the thickness of the second filter region 121, such as at least the portion of the support liner 130 that abuts or is positioned proximate to the second filter region 121. In some examples, the thickness of the support liner 130 below the first filter region 117 at the bottom of the light guides 118 (between the first filter region 117 and the second liner layer 155 and/or dielectric material 142) may be the same or substantially similar thickness as the thickness of the support liner 130 extending about the side surfaces of the first filter region 117 (between the first filter region 117 and the first liner layer 154 and/or dielectric material 142).

The support liner 130 may be void of predefined apertures or other voids that would allow a liquid or solution, such as the reaction solution, to flow therethrough. The support liner 130 may also be void of any internal discontinuities, pores, cracks, breaks or the like, or prevent the formation thereof, that would allow a liquid or solution, such as the reaction solution, to flow therethrough. The support liner 130 may thereby be a liquid impervious barrier layer. A liquid impervious layer herein refers to a layer that may prevent any liquid or solution (e.g., the reaction solution) from passing therethrough, such as preventing at least about 99 vol % of the reaction solution in contact with the protection layer 130 at atmospheric pressure from passing therethrough. The support liner 130 may also be chemically inert with respect to the reaction solution such that the reaction solution (which may include a relatively high acidity or relatively high basicity, as described above) does not etch the support liner 130, or etches less than about one (1) angstrom (Å) of the thickness of the support liner 130 per hour at about 100 degrees Celsius and at about atmospheric pressure, when the reaction solution is in contact with the support liner 130. For example, the composition of the support liner 130 may not chemically react, or chemically reacts to only a relatively small degree, with the composition of the reaction solution (which may include a relatively high acidity or relatively high basicity) such that the reaction solution does not etch the support liner 130 or etches less than about one (1) angstrom (Å) of the thickness of the support liner 130 per hour at about 100 degrees Celsius and at about atmospheric pressure when the reaction solution is in contact with the support liner 130. The support liner 130 may thereby comprise an etch resistant layer with respect to the reaction solution (which may include a pH equal to or less than about 5 or a pH equal to or greater than about 8, for example) to prevent the reaction solution from penetrating therethrough (over time) and, ultimately, interacting with and corroding or otherwise interfering with the functioning of the device circuitry 146. The support liner 130 is thereby configured to prevent a liquid or solution (such as the reaction solution) that may penetrate through the reaction structure 126 and the filter material 116 of a light guide 118 to the support liner 130 from interacting with the device circuitry 146.

The support liner 130 may comprise any material that differs from the material of the first liner layer 154 and the first filter material 116, and such that it allows light emitted from the reaction sites 114 to pass therethrough and to the at least one corresponding light sensor 140 via the corresponding light guide 118. For example, the support liner 130 may comprise any material that allows light emitted from the reaction sites 114 of an associated reaction recess 108 that is not filtered by the first and second filter regions 117, 121 to pass therethrough. As explained further below, the support liner 130 may comprise any material that differs from the material of the first liner layer 154 and the first filter material 116 so that an upper portion of the support liner 130 can be selectively removed (e.g., etched) to form the support liner 130 only in the lower or bottom portion of the light guides 118. In some examples, the support liner 130 may comprise an oxide, a nitride, or a combination thereof. In some such examples, the support liner 130 may comprise of SiO2, a metal oxide or a combination thereof.

In some examples, the support liner 130 may comprise material that is chemically inert to the reaction solution. For example, the support liner 130 may comprise any material that does not chemically react, or chemically reacts to only a relatively small degree, with the reaction solution (which may include a pH equal to or less than about 5 or a pH equal to or greater than about 8, for example) such that the reaction solution does not etch the support liner 130 or etches less than about one (1) angstrom (Å) of the thickness of the support liner 130 per hour at about 100 degrees Celsius and at about atmospheric pressure when the reaction solution is in contact with the support liner 130. For example, the support liner 130 may comprise an oxide, a nitride, or a combination thereof. In some examples, the support liner 130 may comprise silicon dioxide, a metal oxide, a metal nitride or a combination thereof. In some examples, the support liner 130 may comprise silicon dioxide, silicon oxynitride, silicon monoxide, silicon carbide, silicon oxycarbide, silicon nitrocarbide, metal oxide, metal nitride or a combination thereof. In some examples, the pH of the reaction solution is greater than or equal to about 8, and the support liner 130 may comprise silicon dioxide, silicon oxynitride, silicon monoxide, silicon carbide, silicon oxycarbide, silicon nitrocarbide, metal oxide, metal nitride or a combination thereof. In some examples, the pH of the reaction solution is less than or equal to about 5, and the support liner 130 comprises silicon carbide, silicon oxycarbide, silicon nitrocarbide, a metal oxide, a metal nitride or a combination thereof.

As discussed above, the light guides 118 may extend from an opening 158 into the device base 125, such as through the dielectric material layers 142 and toward at least one image sensor 140. In particular examples, the light guides 118 are elongated and extend from proximate to at least one corresponding reaction recess 108 from the aperture 158 thereof toward at least one corresponding light sensor 140 within the sensor layer 141. The light guides 118 may extend lengthwise along a central longitudinal axis. The light guides 118 may be configured in a three-dimensional shape that allows and/or promotes the light emitted from the reaction site(s) 112 of at least one corresponding reaction recess 108 to the at least one corresponding light sensor 140, such as substantially cylindrical or frusto-conical shape with a circular opening 158. The longitudinal axis of the light guides 118 may extend through a geometric center of the cross-section. However, other geometries may be used in alternative examples. For example, the cross-section of the light guides 118 may be substantially square-shaped or octagonal. The light guides 118 may comprise a first filter region 117, the second filter region 121 and the support liner 130.

As discussed above and shown in FIGS. 3 and 4, light guides 118 may include the first filter region 117 and the second filter region 121. The first filter region 117 may be frusto-conical, and the second filter region 121 may be an annular sleeve or liner that extends about the first filter region 117 (above the annular support liner or sleeve 130). The first filter region 117 may comprise a first filter material that is configured to filter the excitation light 101 of a first wavelength or a range of wavelengths (and potentially a fourth wavelength or a range of wavelengths), and permit the light emissions of a second wavelength or a range of wavelengths from at least one reaction site 114 of at least one corresponding reaction recess 108 to propagate therethrough and toward at least one corresponding light sensor 140. Similarly, the second filter region 121 may comprise a second filter material that is configured to filter the excitation light 101 of the first wavelength or a range of wavelengths (and potentially the fourth wavelength or a range of wavelengths), and permit the light emissions of a third wavelength or a range of wavelengths from at least one reaction site 114 of the at least one corresponding reaction recess 108 to propagate therethrough and toward the at least one corresponding light sensor 140. In some examples, the first filter region 117 may also filter the light emissions of the third wavelength or a range of wavelengths from the at least one reaction site 114 (i.e., prevent such emitted light from passing therethrough), and/or the second filter region 121 may also filter the light emissions of the second wavelength or a range of wavelengths from the at least one reaction site 114 (i.e., prevent such emitted light from passing therethrough). In other examples, the first filter region 117 may allow the light emissions of the third wavelength or a range of wavelengths from the at least one reaction site 114 to pass therethrough, and/or the second filter region 121 may allow the light emissions of the second wavelength or a range of wavelengths from the at least one reaction site 114 to pass therethrough. Each of the light guides 118 of the array light guides 118 of the device 104 may include substantially the same configuration (e.g., filtering properties) of the first and second filter regions 117, 121, or differing light guides 118 may include differing configurations (e.g., filtering properties) of the first and second filter regions 117, 121.

The first filter region 117 and the second filter region 121 of the light guide 118 may be, for example, absorption filters (e.g., an organic absorption filter) such that they absorb a respective wavelengths or ranges of wavelengths and allow at least one predetermined wavelength or range of wavelengths to pass therethrough. By way of an example only, at least one first reaction site 114 of at least one reaction recess 108 of the device 104 may be configured to produce first light emissions of a first wavelength or range of wavelengths upon incident excitation light 101 of a third wavelength or range of wavelengths, and at least one second reaction site 114 of at least one reaction recess 108 of the device 104 may be configured to produce second light emissions of a second wavelength or range of wavelengths upon incident excitation light 101 of the third wavelength or range of wavelengths that differs (or does not overlap) from the first light emissions. The first and second reaction sites 114 may be the same reaction site 114, may be differing reaction sites 114 provided within a common reaction recess 108, or may be may be differing reaction sites 114 provided within differing reaction recesses 108. In such an example, the first filter region 117 may absorb the excitation light 101 and the second light emissions, but allow the first light emissions from the first reaction sites to pass therethrough. Similarly, the second filter region 121 may absorb the excitation light 101 and the first light emissions, but allow the second light emissions from the first reaction sites to pass therethrough.

By way of another example, at least one first reaction site 114 of at least one reaction recess 108 of the device 104 may be configured to produce first light emissions of a first wavelength or range of wavelengths upon incident first excitation light 101 of a third wavelength or range of wavelengths, and at least one second reaction site 114 of at least one reaction recess 108 of the device 104 may be configured to produce second light emissions of a second wavelength or range of wavelengths upon incident second excitation light 101 of a fourth wavelength or range of wavelengths. The first, second, third and fourth wavelengths or ranges of wavelengths may differ (and not overlap, if ranges of wavelengths). The third and fourth excitation light 101 may be emitted at the same time (e.g., during the same light detection event), or the third and fourth excitation light 101 may be independently or separately emitted at differing times (e.g., during differing light detection events). The first and second reaction sites 114 may be the same reaction site 114, may be differing reaction sites 114 provided within a common reaction recess 108, or may be may be differing reaction sites 114 provided within differing reaction recesses 108. In such an example, the first filter region 117 may absorb at least the first excitation light 101 and the second light emissions, but allow the first light emissions from the first reaction sites to pass therethrough. The first filter region 117 may also absorb the second excitation light 101. Similarly, the second filter region 121 may absorb at least the second excitation light 101 and the first light emissions, but allow the second light emissions from the first reaction sites to pass therethrough. The second filter region 121 may also absorb the first excitation light 101.

The material of the first and second filter regions 117, 121 may be any material that prevents the excitation light from passing therethrough (e.g., reflects, refracts and/or absorbs such light) and allows emitted light (from at least one reaction site 114) of a predefined or predetermined wavelength or range of wavelengths therethrough. For example, the material of the first and second filter regions 117, 121 may be a polymer material (the same polymer material or a different polymer material) with different dyes. For example, the material of the first and second filter regions 117, 121 may be a polymer material (the same polymer material or a different polymer material) with different dyes. In such examples, the polymer material may include a C—H—O based matrix, and the differing dyes may be differing metal organic complex molecules, for example. However, any other appropriate material may be used. As discussed above, in some examples the first and second filter regions 117, 121 may allow emitted light (from at least one reaction site 114) of differing wavelengths or ranges of wavelengths from passing therethrough. As such, in some examples the first filter region 117 of a light guide 118 may filter (i.e., block) emitted light (from at least one reaction site 114) that the second filter region 121 of the light guide 118 allows to pass therethrough, and/or the second filter region 121 of a light guide 118 may filter (i.e., block) emitted light (from at least one reaction site 114) that the first filter region 117 of the light guide 118 allows to pass therethrough.

Each light guide 118 may thereby be configured relative to surrounding material of the device base 125 (e.g., the dielectric material 142 and/or the first and second liner layers 154, 155) to form a light-guiding structure. For example, the light guides 118 may have a refractive index of at least about 2. In certain examples, the light guide 118 is configured such that the optical density (OD) or absorbance of the excitation light is at least about 4 OD. More specifically, the filter material 116 of the light guides 118 may be selected and the light guide 118 may be dimensioned to achieve at least about 4 OD. In more particular examples, the light guide 118 may be configured to achieve at least about 5 OD, or at least about 6 OD.

Initially, the reaction sites 114 of one or more reaction recesses 108 of the reaction structure 126 of the device 104 or bio assembly 100 may not include a designated reaction. As discussed above, a reaction site 114 may include biological or chemical substances immobilized to the detector surface 112 or, more specifically, on the base and/or side surfaces of the reaction recesses 108. In particular examples, the reaction sites 114 are located proximate to an opening 158 of at least one corresponding light guide 118 so that pre-designated light emissions emitted from the reaction sites 114 after a designated reaction has taken place (via treatment with the reaction solution) propagate through the reaction structure 126, through the opening 158 and the first and/or second filter material 116, 115, through the support liner 130 (and potentially the first and/or second liner layers 154, 155), and to at least one corresponding light sensor 140.

The biological or chemical substances of a single reaction site 114 may be similar or identical (e.g., a colony of analytes (e.g., oligonucleotides) that have a common sequence). However, in other examples, a single reaction site 114 and/or reaction recess may include differing biological or chemical substances. Similarly, reaction sites 114 of a single reaction recess 108 may include different biological or chemical substances (and thereby designated reactions, with differing fluorescent labels). Before a designated reaction, the reaction sites 114 may include at least one analyte (e.g., an analyte-of-interest). For example, the analyte may be an oligonucleotide or a colony thereof (e.g., an oligonucleotide-of-interest). The oligonucleotides may have an effectively common sequence and bind with a predefined or particular fluorescently labeled biomolecule, such as a fluorescently-labeled nucleotide. Different reaction sites 114 may thereby include differing fluorescently labeled biomolecules, such as differently fluorescently-labeled nucleotides.

Figure 5:
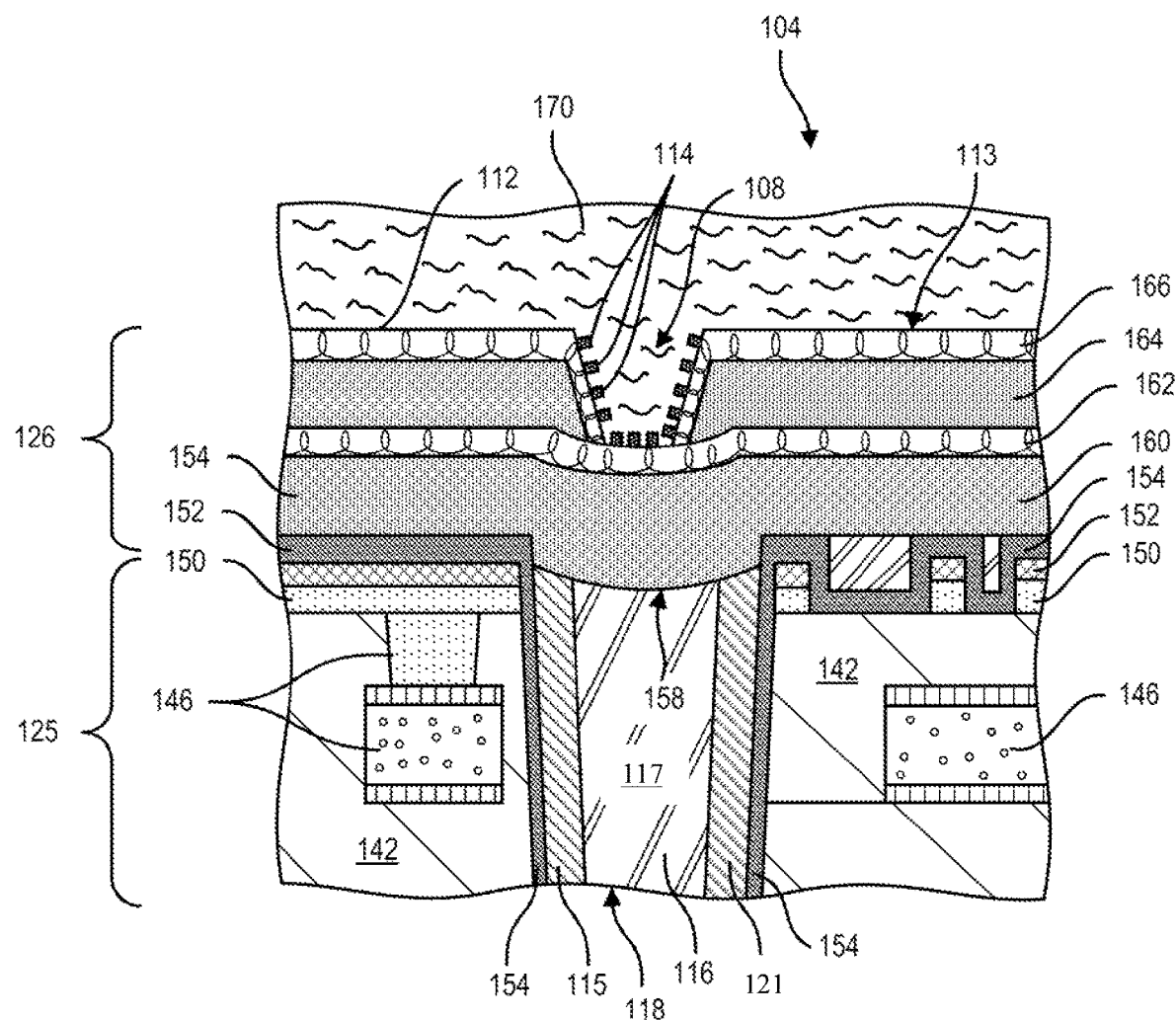
FIG. 5 illustrates, in one example, an enlarged portion of the cross-section of FIG. 3 comprising a reaction solution on the reaction structure.

However, prior to the designated reaction, the fluorophores of the fluorescently labeled biomolecule are not incorporated or bonded to the biological or chemical substances (e.g., an oligonucleotides) at the reaction sites 114. To achieve or obtain a designated reaction (i.e., to incorporate the fluorescently labeled biomolecule with the biological or chemical substances at/of the reaction sites 114), a flow cell may provide a flow of reaction solution 170 to the reaction structure 126 of the light detection device 104, as shown in FIG. 5. In this way, the reaction solution 170 may initiate a reaction and/or form a reaction product at the reaction sites 114 that generates light emissions upon incident excitation light.

The reaction solution may comprise one or more sequencing reagents utilized for DNA grafting, clustering, cleaving, incorporating and/or reading, for example. However, the reaction solution may be any solution. For example, the reaction solution 170 may be an aqueous solution and/or may be comprised of an oil; however, it is understood that the reaction solution 170 may comprise any other liquid. The reaction solution 170 may include one or more constituents that would tend to react with, corrode, dissolve, deteriorate or otherwise render the circuitry 146 inoperable or less effective as circuitry (i.e., transferring signals or electrons). For example, the reaction solution 170 may be an aqueous solution that would tend to oxidize the metal portions of the circuitry 146 if it interacted therewith.

In one example, the reaction solution 170 contains one or more nucleotide types, at least some of which are fluorescently-labeled, and the reaction solution 170 also contains one or more biomolecules, such as polymerase enzymes, which incorporate nucleotides into a growing oligonucleotide at the reaction site 114, thereby labeling the oligonucleotide with a fluorescently-labeled nucleotide. In this implementation, the flow cell provides a wash solution to remove any free nucleotides that did not get incorporated into oligonucleotides. The reaction sites 114 are then illuminated with an excitation light 101 of a first wavelength, causing fluorescence of a second or third wavelength in those reaction sites 114 where a fluorescently-labeled nucleotide was incorporated. Reaction sites 114 that did not incorporate a fluorescently-labeled nucleotide do not emit light.

As shown in the illustrated example in FIG. 5, the reaction solution 170 may be provided within the retraction recesses 118 to achieve the designated reactions, such as at least one fluorescently-labeled molecule binding or incorporating with the biological or chemical substances immobilized at the reaction sites 114. In some examples, the biological or chemical substances of the reaction sites 114 may be an analyte, and the fluorescently-labeled molecule may include at least one fluorophore that bonds or incorporates with the analyte. In such examples, the analyte may comprise an oligonucleotide, and the at least one fluorescently-labeled molecule comprises a fluorescently-labeled nucleotide. The reaction solution 170 may include differing fluorescently-labeled molecules that emit light of differing wavelengths or ranges of wavelengths in response to incident excitation light. Differing reaction sites 114 (of the same or differing reaction recesses 108) may thereby be configured to emit light of differing wavelengths or ranges of wavelengths in response to incident excitation light.

When the biological or chemical substances (e.g., oligonucleotides) of the reaction sites 114 are similar or identical, such as having a common sequence, the reaction sites 114 may be configured to generate common light emissions after the designated reaction and the excitation light 101 is absorbed by fluorescently-labeled molecules bonded or incorporated therewith from the reaction solution 170. When biological or chemical substances (e.g., oligonucleotides) of the reaction sites 114 are different, such as having different sequences, the reaction sites 114 may be configured to generate different light emissions (different wavelengths or ranges or wavelengths) after the designated reactions and the excitation light 101 is absorbed by differing fluorescently-labeled molecules bonded or incorporated therewith (e.g., provided by the reaction solution 170). In this way, the first filter region 117 of the light guides 118 may be selected or configured to allow light emissions from reaction sites 114 with a first designated reaction to propagate therethrough and to the corresponding light sensor 140 (and prevent the excitation light, and potentially light emissions from reaction sites 114 with second designated reactions, from passing therethrough to the corresponding light sensor 140), and the second filter region 121 of the light guides 118 may be selected or configured to allow light emissions from reaction sites 114 with a second designated reaction that differs from the first designated reaction (e.g., including different fluorescently-labeled molecules that emit light of differing wavelengths or ranges of wavelengths) to propagate therethrough and to the corresponding light sensor 140 (and prevent the excitation light, and potentially light emissions from reaction sites 114 with the first designated reactions, from passing therethrough to the corresponding light sensor 140).

Figure 6:
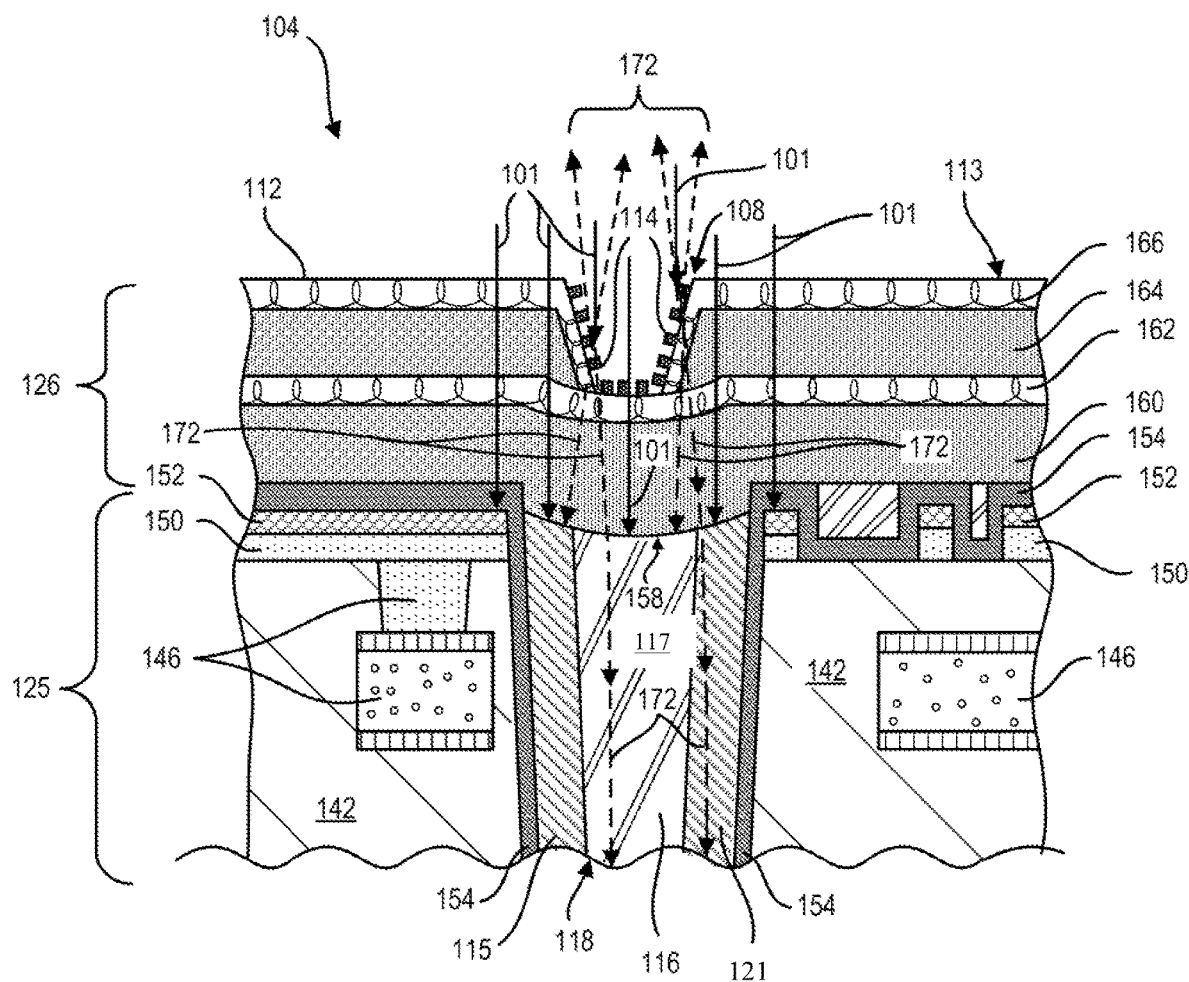
FIG. 6 illustrates, in one example, an enlarged portion of the cross-section of FIG. 3 comprising a light detection event.

As shown in FIG. 6, after the reaction solution 170 has interacted with the biological or chemical substances (e.g., oligonucleotides) of the reaction sites 114, the designated reactions have occurred such that the reaction sites 114 include fluorescently-labeled molecules (the same or different fluorescently-labeled molecules), such as fluorophores, that emit light of a predefined or predetermine wavelength or range of wavelengths when excited by the excitation light 101 (i.e., when the excitation light 101 is incident upon the reaction sites 114). The excitation light 101 may thereby be configured based on the fluorescently-labeled molecules of the reaction solution 170, or vice-versa. As shown in FIG. 6, when excited by the excitation light 101, the reaction sites 114 may emit emitted light 172 or signals of a wavelength or range of wavelengths that differs from excitation light 101.

As shown in FIG. 6, the emitted light 172 from the reaction sites 114 may emit in all directions (e.g., isotropically) such that, for example, a portion of the emitted light 172 is directed into the at least one corresponding light guide 118, and a portion of the light 172 is directed into the flow channel 119 or the reaction structure 126. For the portion that is directed into the light guide 118, the devices 104 is configured to facilitate detection of the photons by the at least one corresponding light sensor 140. Specifically, the emitted light 172 from the reaction sites 114 that passes through the opening 158 of a corresponding light guide 118 will propagate through the first or second filter region 117, 121 thereof to the light sensor 140. The excitation light 101, however, will be absorbed or otherwise prevented from propagating through the light guide 118 to the light sensor 140 by the first and/or second filter region 117, 121, as shown in FIG. 6.

As shown in FIG. 6, some of the reaction sites 114 may be configured to emit light 172 of a first wavelength or range of wavelengths that is not filtered by the first filter region 117 but is filtered (i.e., prevented from passing through) by the second filter region 121, and some of the reaction sites 114 may be configured to emit light 172 of a second wavelength or range of wavelengths that is not filtered by the second filter region 121 but is filtered (i.e., prevented from passing through) by the first filter region 117. As noted above, in some examples some reaction sites 114 of the device 104 may be configured to emit light 172 of the first wavelength or range of wavelengths upon incident excitation light 101 of a third wavelength, and some other reaction sites 114 of the device 104 may be configured to emit light 172 of the second wavelength or range of wavelengths upon the incident excitation light 101 of the third wavelength. In such an example, the first and second filter regions 117, 121 may both be configured to filter the excitation light 101 of the third wavelength. Still further, in some other examples some reaction sites 114 of the device 104 may be configured to emit light 172 of the first wavelength or range of wavelengths upon incident excitation light 101 of a third wavelength or range of wavelengths, and some other reaction sites 114 of the device 104 may be configured to emit light 172 of the second wavelength or range of wavelengths upon the incident excitation light 101 of a fourth wavelength or range of wavelengths. In such an example, the first and second filter regions 117, 121 may both be configured to filter the excitation light 101 of the third and fourth wavelength or ranges of wavelengths, or the first and second filter regions 117, 121 may be configured to filter one of the excitation light 101 of the third and fourth wavelengths or ranges of wavelengths (e.g., the first filter region 117 may be configured to filter the excitation light 101 of the third wavelength or range of wavelengths, and the second filter region 121 may be configured to filter the excitation light 101 of the fourth wavelength or range of wavelengths). The device circuitry 146 that is electrically coupled to the light sensors 140 transmits data signals based on the photons detected by the light sensors 140. In this way, only the presence of a designated reaction at a reaction site 114 via treatment with the reaction solution will cause emitted light 172 to be detected by the light sensors 140 during a light detection even (i.e., a reaction that results in emittance light 172 that is not filtered by at least one of the first and second filter regions 117, 121).

As shown in FIG. 6, a portion of the emitted light 172 from the reaction sites(s) 114 that passes into the at least one corresponding light guide 118 may propagate directly through the first filter material 117 or the second filter material 115 thereof and to the at least one corresponding light sensor 140. For example, at least a majority of the emissive light 172 from the reaction sites(s) 114 that passes into the at least one corresponding light guide 118 via the opening 158 may pass directly (e.g., linearly or substantially linearly) through the first filter material 117 or the second filter material 115 to the at least one corresponding light sensor 140. A small amount of the emissive light 172 from the reaction sites(s) 114 that passes into the at least one corresponding light guide 118 may travel at an angle such that it passes through the support liner 130, the liner layer 154 and into the dielectric material layers 142. Such light may be reflected by the circuitry 146 or other metal or reflective structures embedded within the dielectric material layers 142, and potentially back into the corresponding light guide 118 (and potentially to the at least one corresponding light sensor 140). In some examples, the support liner 130 and/or the liner layer 154 may be transparent to light, such as transparent or substantially transparent at least to the emissive light 172 from the reaction sites(s) 114.

FIGS. 7-13 illustrates an example of a method 200 of manufacturing a light detection device, such as the light detection device 104 of FIGS. 1-6. Therefore, like reference numerals preceded with "2," as opposed to "1," are used to indicate like components, aspects, functions, processes or functions, and the description above directed thereto equally applies, and is not repeated for brevity and clarity purposes. The method 200, for example, may employ structures or aspects of various examples (e.g., systems and/or methods) discussed herein. In various examples, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

Figure 7:
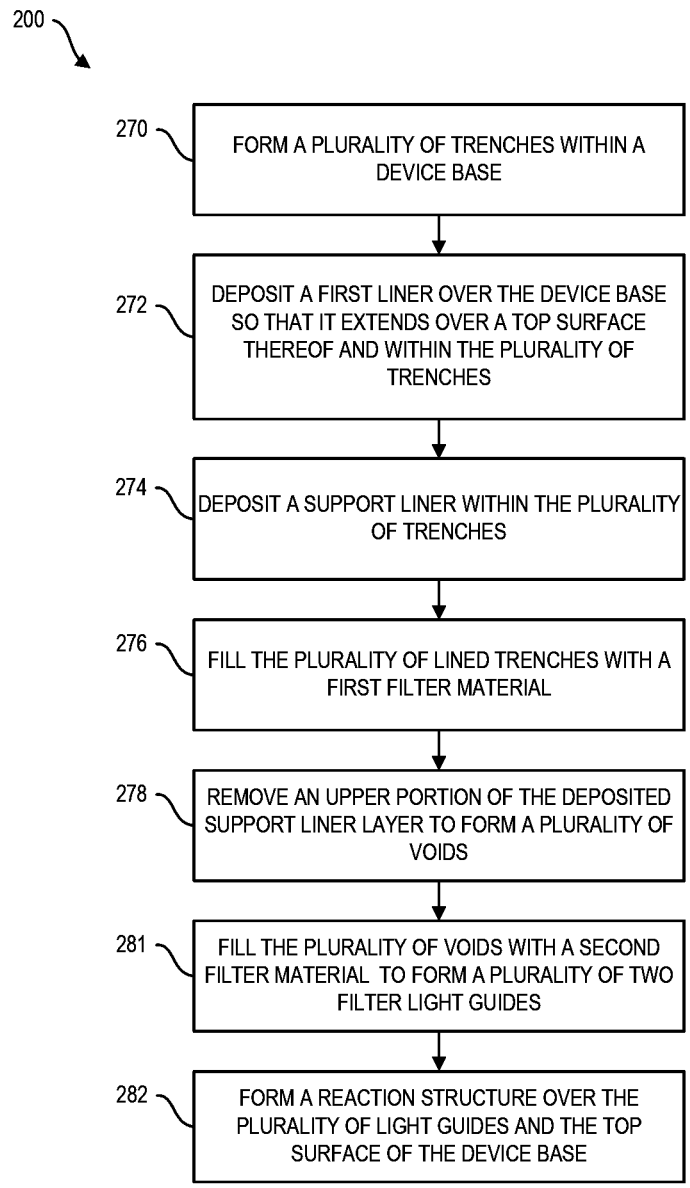
FIG. 7 is a flowchart illustrating, in one example, a method of manufacturing a biosensor in accordance with the present disclosure.
Figure 8:
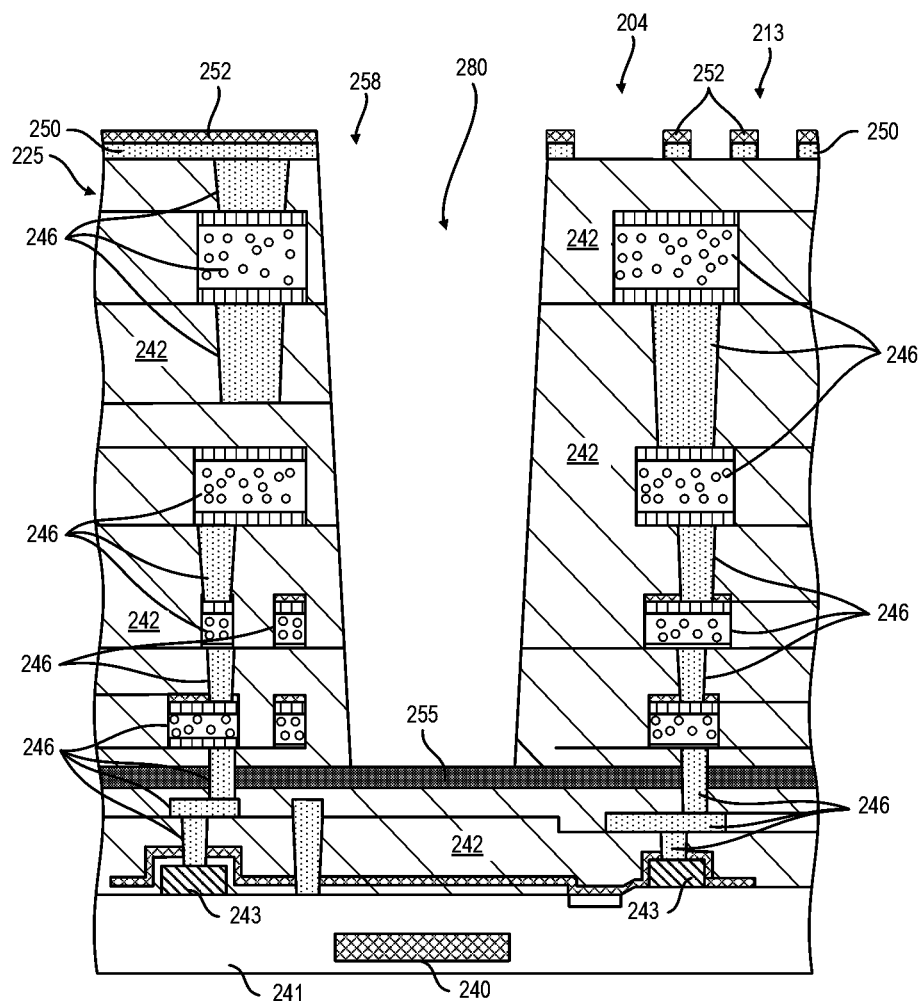
FIG. 8 illustrates, in one example, the formation of a trench in a light detection device base.

As shown in FIGS. 7 and 8, the method 200 of forming a device 204 may include forming (at 270 of FIG. 7) a plurality or array of trenches or cavities 280 within a device base 225. As discussed above, the device base 225 may include an array of light sensors 240 and device circuitry 246 electrically coupled to the light sensors 240 that transmit data signals based on photons detected by the light sensors 240. The device base 225 may be provided or obtained via any process. For example, the device base 225 may be obtained in a preassembled or premanufactured state, or the device base 225 may be formed or manufactured prior to forming 270 the plurality of trenches 280. The plurality of trenches may extend from an outer, external or top surface of the device base 225 and toward at least one corresponding light sensor 240 (through the thickness of the device base 225).

As discussed above, the device base 225 may be manufactured using integrated circuit manufacturing technologies, such as CMOS manufacturing technologies. For example, the device base 225 may include several substrate layers (e.g., dielectric material layers 242) with different modified features (e.g., metallic elements) embedded therein that form the device circuitry 246. The plurality of trenches 280 may be formed in the substrate layers (e.g., in the dielectric material layers 242) to correspond to portions of the device base 225 that will include, after the method 200, the light guides 218. While only one trench 280 is depicted in FIG. 8, as described above the device base 225 may include an array of light guides 218, and therefore an array of trenches 280 may be formed.

As shown in FIG. 8, the trenches 280 may extend through openings in the first shield layer 250 and/or second shield layer 252 and through the dielectric material 242 toward at least one corresponding light sensor 240. As shown in FIG. 8, interior surfaces of the device base 225, such as the dielectric material 242 thereof, may define the trenches 280 for the formation of the light guides 218 therein. The trenches or cavities 280 may extend to the second liner layer 255 that extends through the dielectric material 242. In this way, the second liner layer 255 may form the bottom of the trenches 280. As also shown in FIG. 8, other openings in the first shield layer 250 and/or second shield layer 252 may be formed in the interstitial areas 213 of the device base 225.

The trenches 280 may be formed by any process(es) or technique(s) that removes the portions of the dielectric material 242 (and potentially portions of the first shield layer 250 and/or second shield layer 252). For example, the trenches 280 may be formed by one or more selective etching processes and/or reactive ion etching process. In one example, the trenches 280 may be formed by applying at least one mask (not shown) to the device base 225 and removing material (e.g., through etching) of the portions of the dielectric material 242 (and potentially portions of the first shield layer 250 and/or second shield layer 252).

Figure 9:
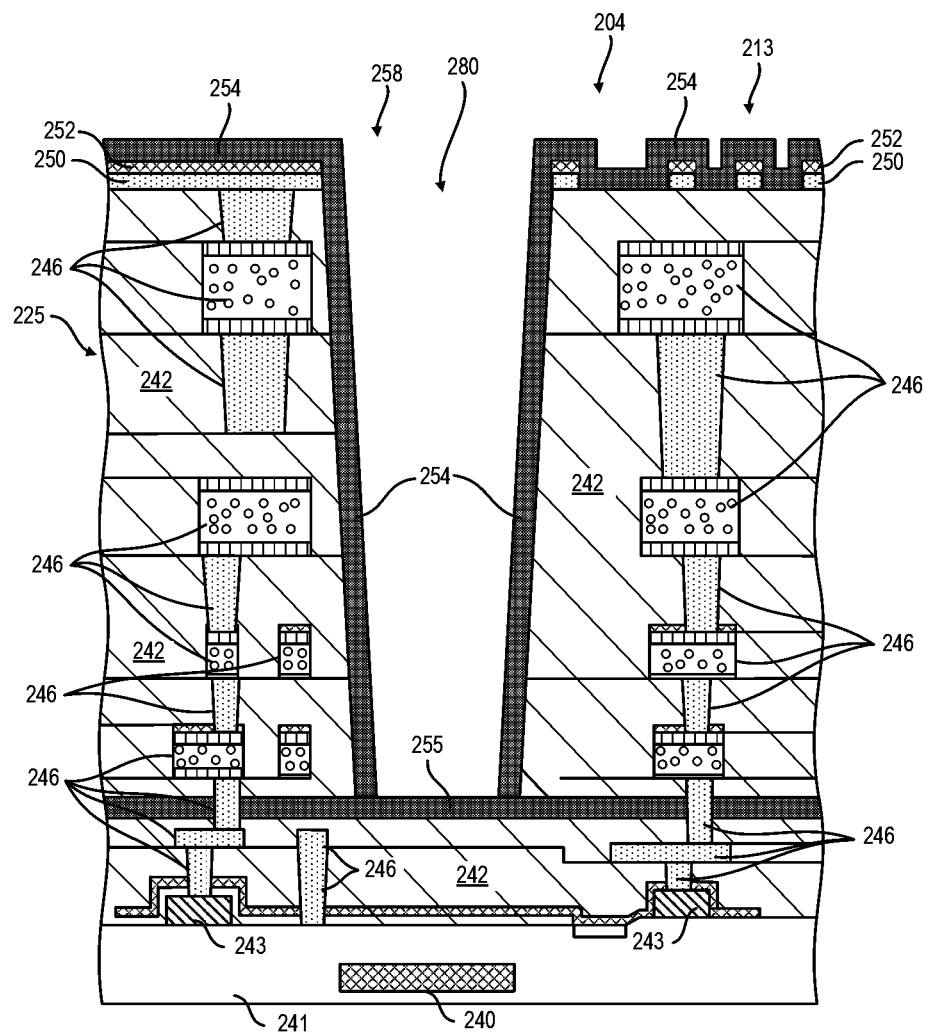
FIG. 9 illustrates, in one example, the formation of a first liner within the trench in the device base of FIG. 8.

As shown in FIGS. 7 and 9, after formation of the plurality of trenches 280, the method 200 may include depositing (at 272 of FIG. 7) the first liner layer 254 over the top surface of the device base 225 and within the plurality of trenches 280. In some examples, the first liner layer 254 may be formed over the sidewalls of the plurality of trenches 280 and not over the second liner layer 255 at the bottom of the trenches 280. In some other examples, the first liner layer 254 may be formed over the second liner layer 255 at the bottom of the trenches 280, but then subsequently removed. The first liner layer 254 may be deposited over the second shield layer 252 on the top surface of the device base 225, and potentially over any openings in the openings in the first shield layer 250 and/or second shield layer 252 in interstitial areas 213 of the device base 225 such that the second shield layer 252 extends over the dielectric material 242 in such openings, as shown in FIG. 9.

The first liner layer 254 may be configured as an anti-reflective layer or a reflective layer (e.g., to ensure the light emitted from reaction sites passes through the light guides), a contamination prevention layer (e.g., to prevent sodium contamination of the circuitry) and/or an adhesion layer (e.g., to adhere filter material of the light guides to the dielectric material). In some examples, the first liner layer 254 may be configured as a contamination prevention layer that prevents any ionic species from penetrating into device layers (e.g., metal-dielectric layers). In some examples, the first liner layer 254 may comprise SiN.

The first liner layer 254 may be a continuous conformal layer formed on the device base 225. The first liner layer 254 may be void of defined apertures. However, the first liner layer 254 may include at least one internal discontinuity, pore, crack, break or the like that allows a liquid or solution, such as the reaction solution, to flow through the first liner layer 254. For example, the density of the first liner layer 254 may be relatively low such that internal discontinuities thereof form a pathway through the first liner layer 254. As another example, discontinuities extending through the first liner layer 254 may be formed by the reaction solution or any other liquid or solution) from reacting with and etching through the first liner layer 254. The discontinuities of the first liner layer 254 may allow a liquid or solution (e.g., the reaction solution) from passing therethrough and, ultimately, to the conductive (e.g., metal) components of the device circuitry 246. As discussed above, the liquid or solution (e.g., the reaction solution may corrode or otherwise interfere with the operation of the device circuitry 246.

The first liner layer 254 may be formed by any process(es) or technique(s). For example, the first liner layer 254 may be formed by at least one chemical deposition process (e.g., plating, chemical vapor deposition (CVD), plasma enhanced CVD (PECVD), or atomic layer deposition (ALD), for example), a physical deposition process, a growth mode, epitaxy, or a combination thereof. In some examples, the first liner layer 254 may be formed conformally over the surface of the device base 225 and within the trenches 280 (e.g., over the side walls and, potentially, the bottom surface of the trenches 280). The first liner layer 254 may comprise a substantially constant thickness, or the thickness may vary.

After formation of the first liner layer 254 on the device base 225 (and within the trenches 280), the first liner layer 254 may be further processed. For example, at least the portion of the first liner layer 254 extending over the top surface of the device base 225 (i.e., the interstitial areas 213 of the first liner layer 254) may be processed to planarize, flatten, smooth or otherwise improve the surface topography thereof. In some such examples, at least the portion of the first liner layer 254 extending over the top surface of the device base 225 (i.e., the interstitial areas 213 of the first liner layer 254) may be etched and/or polished (e.g., chemical and/or mechanical polishing/planarization) to planarize the outer surface of the first liner layer 254.

Figure 10:
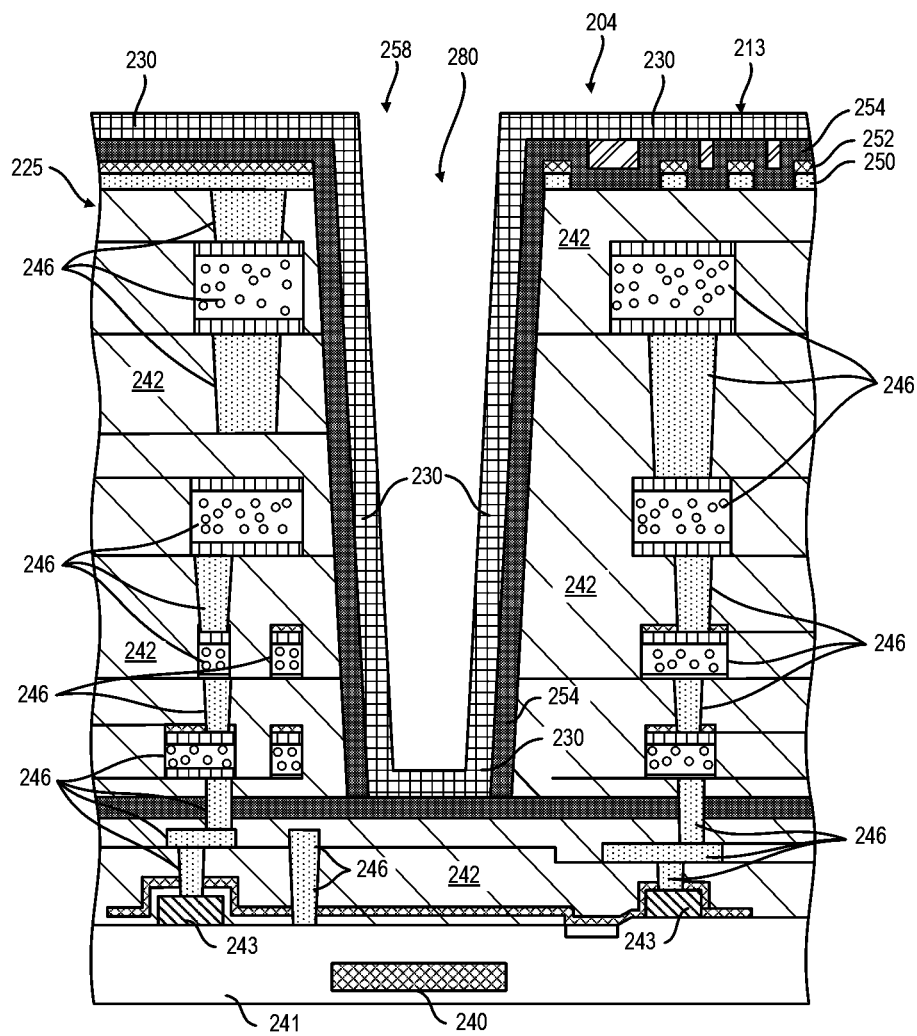
FIG. 10 illustrates, in one example, the formation of a second liner within the trench of the device base of FIG. 9.

As shown in FIGS. 7 and 10, the method 200 may include depositing (at 274 of FIG. 7) the support liner 230 over the device base 225 such that it extends over the top surface of the device base 225 and within the plurality of trenches 280. In some examples, the support liner 230 may be formed over the sidewalls of the plurality of trenches 280 and the bottom of the trenches 280. The support liner 230 may be formed over the first liner layer 254 and the second liner layer 255.

The support liner 230 may be formed by any process(es) or technique(s). For example, the support liner 230 may be formed by at least one chemical deposition process (e.g., plating, chemical vapor deposition (CVD), plasma enhanced CVD (PECVD), or atomic layer deposition (ALD), for example), a physical deposition process, a growth mode, epitaxy, or a combination thereof. In some examples, the support liner 230 may be formed conformally over the surface of the device base 225 and within the trenches 280 (e.g., over the side walls and, potentially, the bottom surface of the trenches 280). The support liner 230 may comprise a substantially constant thickness, or the thickness may vary. As discussed further below, the support liner 230 may comprise differing material than the material of the first filter region 217.

As discussed above, the support liner 230 may be configured such that it forms a solid continuous barrier layer (without voids, cracks or other discontinuities) that prevents any reaction solution (which may include a pH equal to or less than about 5 or a pH equal to or greater than about 8, for example) that penetrates through the reaction structure 226, and potentially through the filter material 216 of the light guides 218, from interacting with the circuitry 246. For example, the support liner 230 may be configured such that it is chemically inert with respect to the reaction solution such that the reaction solution (which may include a relatively high acidity or relatively high basicity, as described above) does not etch the support liner 230, or etches less than about one (1) angstrom (Å) of the thickness of the support liner 230 per hour at about 100 degrees Celsius and at about atmospheric pressure, when the reaction solution is in contact with the support liner 230. For example, the support liner 230 may comprise an oxide, a nitride, or a combination thereof. In some examples, the support liner 230 may comprise silicon dioxide, a metal oxide, a metal nitride or a combination thereof. In some examples, the support liner 230 may comprise silicon dioxide, silicon oxynitride, silicon monoxide, silicon carbide, silicon oxycarbide, silicon nitrocarbide, metal oxide, metal nitride or a combination thereof. In some examples, the pH of the reaction solution is greater than or equal to about 8, and the support liner 230 comprises silicon dioxide, silicon oxynitride, silicon monoxide, silicon carbide, silicon oxycarbide, silicon nitrocarbide, metal oxide, metal nitride or a combination thereof. In some examples, the pH of the reaction solution is less than or equal to about 5, and the support liner 230 comprises silicon carbide, silicon oxycarbide, silicon nitrocarbide, a metal oxide, a metal nitride or a combination thereof. The support liner 230 may thereby prevent the reaction solution of any other solution or liquid from interacting with (and thereby deteriorating) the device circuitry 246. The method of formation, thickness and material of the support liner 230 may be configured, independently or in consideration of each other, so that the support liner 230 is void of any discontinuities that would allow any solution or liquid (e.g., the reaction solution) from passing therethrough, and the support liner 230 is chemically inert with respect to the reaction solution such that support liner 230 is etch resistant (by the reaction solution).

Figure 11:
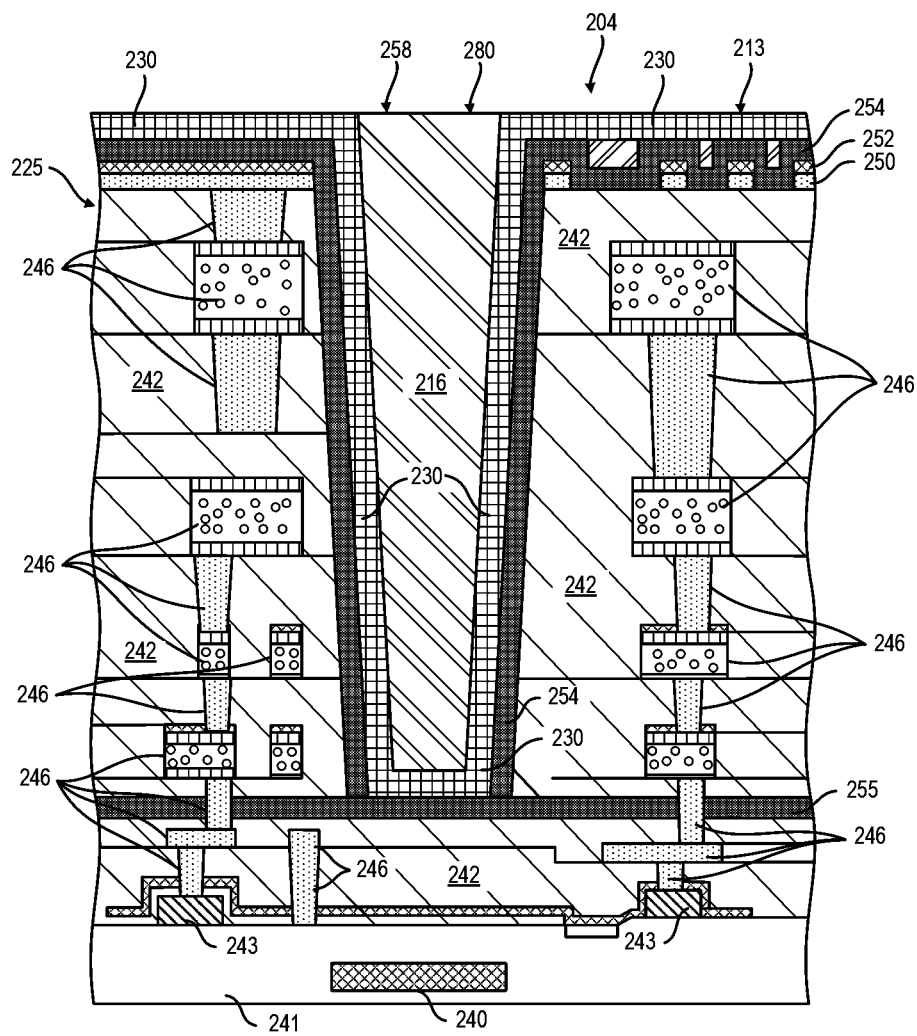
FIG. 11 illustrates, in one example, filling the lined trench of FIG. 10 with first filter material to form a first filter region.

As shown in FIGS. 7 and 11, after formation of the support liner 230, the method 200 may include filling (at 276 of FIG. 7) the plurality of lined trenches 280 with at least one first filter material to form the first filter region 217 of the plurality of light guides 218. As discussed above, the at least one filter material 216 may filter light of a first wavelength or range of wavelengths (e.g., the excitation light), and permits light of a second wavelength or range of wavelengths (e.g., emitted light from first reaction sites) to pass therethrough to at least one corresponding light sensor 240. In some examples, the amount of the filter material 216 applied to the device base 225 may exceed the available volume within the lined trenches 280. As such, the first filter material 216 may overflow the lined trenches 280 and extend along the top of the device base 225, such as over the support liner 230. In such an example, at least the portion of the first filter material 216 extending over the top surface of the support liner 230 may be removed. In alternative examples, the filling operation 276 may include selectively filling each lined trench 280 such that the first filter material 216 does not clear or overflow the trench 280 (e.g., does not extend over the top of the support liner 230 or the first liner layer 254). In some examples, filling (at 276 of FIG. 7) the first filter material 216 may include mechanically pressing or forcing the first filter material 216 at least into the lined trenches 280.

Figure 12:
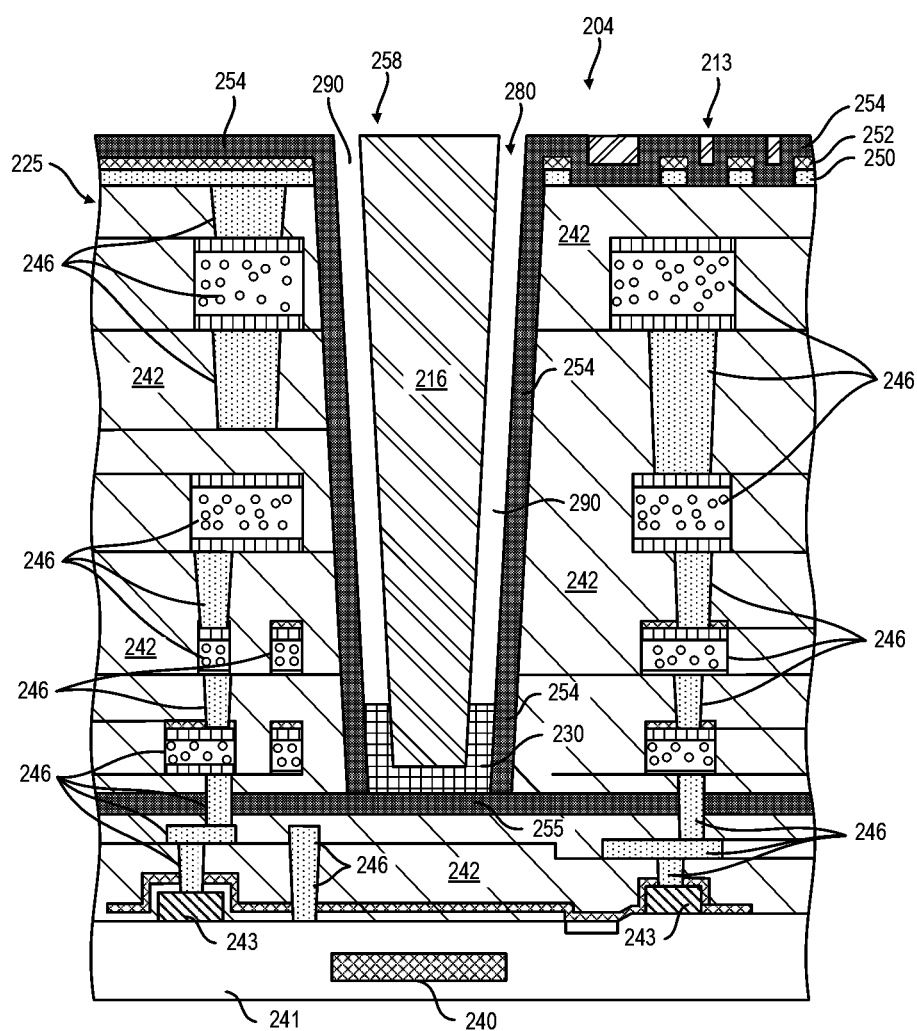
FIG. 12 illustrates, in one example, the removal of an upper portion of the second liner to form a cavity within the trench of the device base of FIG. 11.

As shown in FIGS. 7 and 12, after deposition of the first filter material 216 within the lined the trenches 280, the method 200 may include selectively removing (at 278 of FIG. 7) an upper portion of the support liners 230 to form a void, gap, cavity or open space 290 extending about the first filter material 216 and between the first filter material 216 and the dielectric material 142 (and the first liner layer 254, if present) of each trench 280, as shown in FIG. 12. The voids 290 may extend from the top surface of the device base 225 (thus forming openings at the top surface of the device base 225) to the remaining or non-removed bottom portion of the support liners 230. The void 290 within the guides 218 may thereby be annular, and extend from a bottom portion of the trenches 280 to the top surface of the device base 225.

As shown in FIG. 12, a bottom or lower portion of the support liner 230 may not be removed and may remain within the trench 280 below the first filter material 216 and about a bottom or lower portion of the first filter material 216. In this way, after selective removal of the top portion of the support liner 230, the first filter material 216 may be a free-standing member (e.g., frusto-conically shaped) that is supported by the support liner 230 at its base or bottom portion.

The upper portion of the support liner 230 may be selectively removed such that the first filter material 216 deposited within the trenches 280 remains fully, or at least substantially, intact. Similarly, the upper portion of the support liner 230 may be selectively removed such that the first liner layer 254 deposited within the trenches remains fully, or at least substantially, intact. If the device base 225 does not include the first liner layer 254 within the trenches 280, the upper portion of the support liner 230 may be selectively removed such that the dielectric material 242 adjacent to the trenches 208 remains fully, or at least substantially, intact. The upper portion of the support liner 230 may be removed via any selective removal process that only removes the upper portion of the support liner 230. As discussed above, the material of the support liner 230 may differ from the first liner layer 254 (and the dielectric material 242) and the material of the first filter region 217. In some such examples, the upper portion of the support liner 230 may be removed via at least one selective chemical or plasma etch process that is material-specific to the support liner 230 (and not the first liner layer 254 and the material of the first filter region 217). For example, a radical-based chemical etch process, such as the Producer® Selectra™ etch process of Applied Materials®, may be utilized to selectively remove the upper portion of the support liner 230.

It is noted, however, that in some examples the upper portion of the support liner 230 may not be removed to form the voids 290. Rather, the support liner 230 may remain over the device base 225 such that it extends over the top surface of the device base 225 and within the plurality of trenches 280 extending about the first filer material 216 between the first filter material 216 and the dielectric material and device circuitry 246, as shown in FIG. 11. In such an example, the method 200 may include forming (at 282 of FIG. 7) a reaction structure over the plurality of light guides 218, with only the first filter material 216 and the support liner 230 as shown in FIG. 11, and the interstitial areas 213 of the device base 225 (e.g., over the top surface of the device base 225, such as over the support liner 230), as discussed further below. The support liner 230 can thereby prevent any solution or liquid, such as the reaction solution, that may penetrate through the reaction structure, or the reaction structure and a light guide 218, from ultimately interacting with the device circuitry 246.

Figure 13:
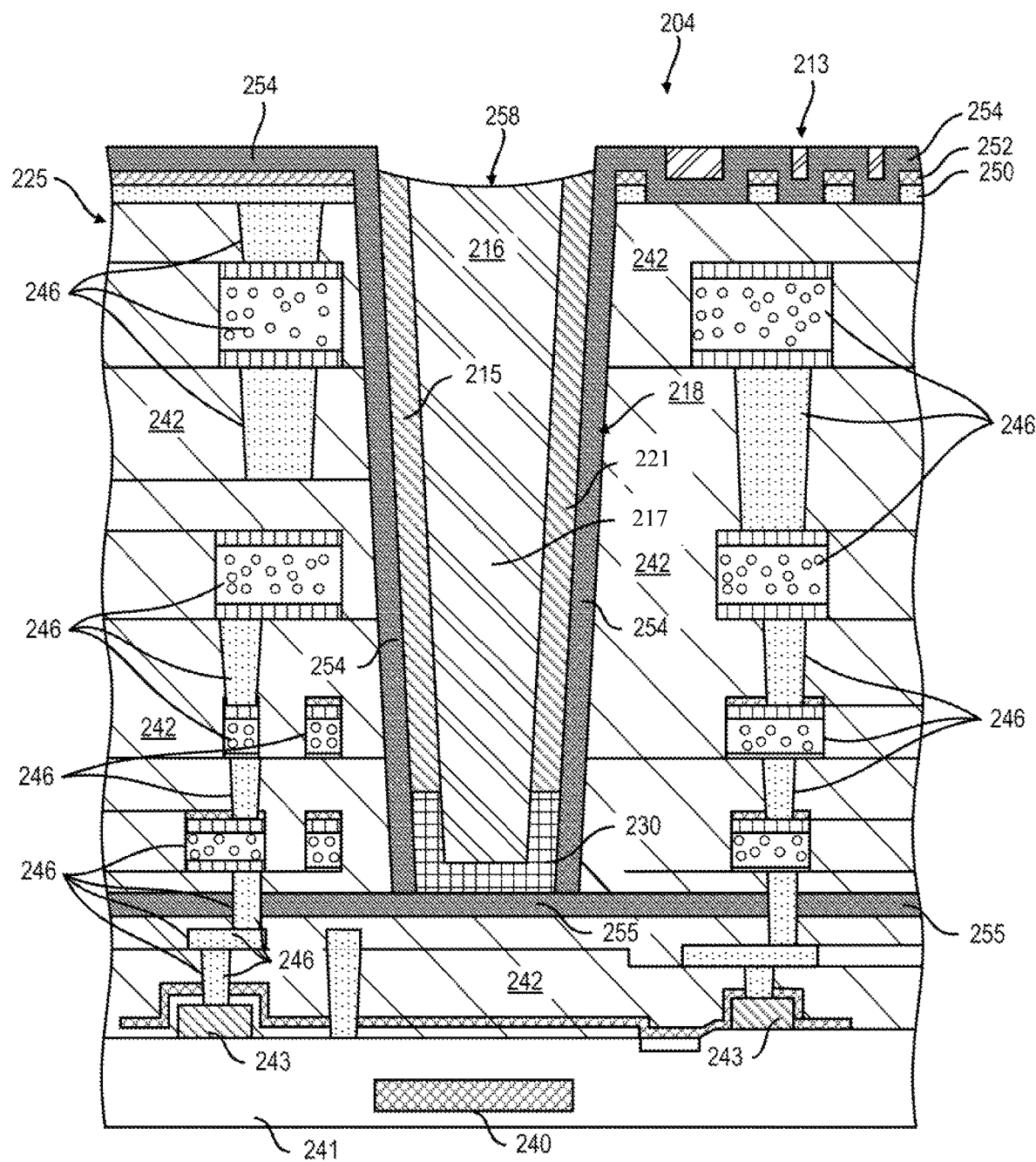
FIG. 13 illustrates, in one example, filling the cavity of the trench of the device base of FIG. 12 with second filter material to form a light guide with first and second filter regions.

If the upper portion of the support liner 230 is selectively removed to form the voids 290 as shown in FIGS. 7 and 13, the method 200 may include filling (at 281 of FIG. 7) the plurality of voids 290 with at least one second material to form the second filter region 221 of the plurality of light guides 218. The first and second filter regions 217, 221 may thereby form the light guides 218. As discussed above, the filter material of the second filter region 221 may filter light of a first wavelength or range of wavelengths (e.g., the excitation light), and permit light of a third wavelength or range of wavelengths (e.g., emitted light from first reaction sites) to pass therethrough to at least one corresponding light sensor 240. As also noted above, the filter material of the second filter region 221 may filter light of a second wavelength or range of wavelengths that the first filter region 117 allows to pass therethrough. In this way, each of the first and second filter regions 217, 221 may filter the wavelength or range of wavelengths that the other region allows to pass therethrough.

In some examples, the amount of the second filter material 215 applied to the device base 225 may exceed the available volume within the voids 290. As such, the second filter material 215 may overflow the voids 290 and extend along the top of the device base 225, such as over the support liner 230. In such an example, at least the portion of the second filter material 215 extending over the top surface of the device base 225 (e.g., over the first liner layer 254) may be removed. In alternative examples, the filling operation 280 of the voids 290 may include selectively filling each void 290 such that the second filter material 215 does not clear or overflow the voids 290 (e.g., does not extend over the top of the device base 225, such as over the first liner layer 254). In some examples, filling (at 280 of FIG. 7) the voids 290 with the second filter material 215 may include pressing (e.g., using a squeegee-like component) the second filter material 215 at least into the voids 290.

Optionally, after formation of the light guides 218 via the first and second filter regions 217, 221, the method 200 may include removing a portion of the first filter material 216 and/or the second filter material 215 from the top portion of the device base 225 (if present) and/or from within the light guides 218, as shown in FIG. 13. The first and second filter material 216, 215 be removed from within the light guides 218 so that the opening 258 of the light guides 218 is located at a depth or position below the top surface of the first liner layer 254 as shown in FIG. 13. Different processes, or the same process, may be implemented for removing one or more portions of the first filter material 216 and/or the second filter material 215. For example, a removal operation may include at least one of etching or chemically polishing portions of the first filter material 216 and/or the second filter material 215.

After formation of the light guides 218 via the first and second filter regions 217, 221, the method 200 may include forming (at 282 of FIG. 7) a reaction structure over the plurality of light guides 218 and the interstitial areas 213 of the device base 225 (e.g., over the top surface of the device base 225, such as over the first liner layer 254) (see FIG. 3). As discussed above, the reaction structure provided over the plurality of light guides 218 and the interstitial areas 213 of the top surface of the device base 225 may include a plurality of reaction recesses each corresponding to at least one light guide 218 for containing at least one reaction site and a reaction solution that initiates a reaction and/or forms a reaction product at the at least one reaction site that generates or emits light in response to incident excitation light. As also discussed above, the reaction structure may comprise a plurality of layers. As such, forming (at 282 of FIG. 7) the reaction structure may include forming a plurality of layers over the device base 225 (e.g., the top surface of the device base 225 and the opening 258 of the light guides 218) (see FIG. 3). The reaction structure may be formed by any process(es) or technique(s).

Optionally, the method 200 may include providing at least one reaction sites in at least one reaction recess of the formed reaction structure and/or mounting a flow cell to the device 204 (see FIG. 1). Providing the reaction sites may occur prior to or after the flow cell is coupled to the device 204. The reaction sites may be positioned at a predetermined pattern along the reaction recesses. The reaction sites may correspond (e.g., one site to one light sensor, one site to multiple light sensors, or multiple sites to one light sensor) in a predetermined manner. In other examples, the reaction sites may be randomly formed along the reaction recesses. As described herein, the reaction sites may include biological or chemical substances immobilized to the detector surface within the reaction recesses. The biological or chemical substances may be configured to emit light signals in response to excitation light. In particular examples, the reaction sites include clusters or colonies of biomolecules (e.g., oligonucleotides) that are immobilized on the detector surface within the reaction recesses.

It is to be understood that the above description is intended to be illustrative, and not restrictive. For example, the above-described examples (and/or aspects thereof) may be used in combination with each other. In addition, many modifications may be made to adapt a particular situation or material to the teachings of the various examples without departing from their scope. While dimensions and types of materials may be described herein, they are intended to define parameters of some of the various examples, and they are by no means limiting to all examples and are merely exemplary. Many other examples will be apparent to those of skill in the art upon reviewing the above description. The scope of the various examples should, therefore, be determined with reference to the appended claims, along with the full scope of equivalents to which such claims are entitled.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

In the appended claims, the terms "including" and "in which" are used as the plain-English equivalents of the respective terms "comprising" and "wherein." Moreover, in the following claims, the terms "first," "second," and "third," etc. are used merely as referee labels, and are not intended to impose numerical, structural or other requirements on their objects. Forms of term "based on" herein encompass relationships where an element is partially based on as well as relationships where an element is entirely based on. Forms of the term "defined" encompass relationships where an element is partially defined as well as relationships where an element is entirely defined. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure. It is to be understood that not necessarily all such objects or advantages described above may be achieved in accordance with any particular example. Thus, for example, those skilled in the art will recognize that the devices, systems and methods described herein may be embodied or carried out in a manner that achieves or optimizes one advantage or group of advantages as taught herein without necessarily achieving other objects or advantages as may be taught or suggested herein.

While this disclosure has been described in detail in connection with only a limited number of examples, it should be readily understood that the disclosure is not limited to such disclosed examples. Rather, this disclosure can be modified to incorporate any number of variations, alterations, substitutions or equivalent arrangements not heretofore described, but which are commensurate with the spirit and scope of the disclosure. Additionally, while various examples have been described, it is to be understood that aspects of the disclosure may include only one example or some of the described examples. Also, while some examples are described as having a certain number of elements, it will be understood that the examples can be practiced with less than or greater than the certain number of elements.

What is claimed is:

1. A device, comprising:
   a plurality of reaction sites;
   a plurality of light sensors; and
   a plurality of light guides with input regions to receive incident excitation light and light emissions from at least one corresponding reaction site, the light guides extending from the input regions toward at least one corresponding light sensor,
   wherein each of the plurality of light guides comprise a first filter region formed of a first filter material to filter the incident excitation light of at least a first wavelength and permit the light emissions of a second wavelength to pass therethrough to the at least one corresponding light sensor, and a second filter region formed of a second filter material to filter the incident excitation light of at least the first wavelength and permit the light emissions of a third wavelength to pass therethrough to the at least one corresponding light sensor,
   wherein the second filter material surrounds the first filter material.

2. The device of claim 1, wherein each of the light guides further comprises a support layer within a bottom portion of the respective light guide extending below and about a bottom portion of the first filter region.

3. The device of claim 2, wherein the support layer is comprised of an oxide, a nitride, or a combination thereof.

4. The device of claim 2, wherein the second filter region of each light guide extends over the corresponding support layer and about the first filter region.

5. The device of claim 4, wherein the first and second filter regions form the input regions of the light guides.

6. The device of claim 2, further comprising device circuitry electrically coupled to the light sensors to transmit data signals based on photons detected by the light sensors.

7. The device of claim 6, further comprising a second liner layer positioned between the support layer and the device circuitry at the bottom portion of the light guides, and positioned between second filter region device circuitry within a top portion of the light guides.

8. The device of claim 7, wherein the second liner layer comprises a silicon nitride shield layer.

9. The device of claim 1, wherein the first filter material further filters the light emissions of the third wavelength.

10. The device of claim 1, wherein the second filter material further filters the light emissions of the second wavelength.

11. The device of claim 1, wherein the first filter material is a polymer material with a first dye, and the second filter material is a polymer material with a second dye that differs from the first dye.

12. The device of claim 1, wherein each of the plurality of reaction sites is immobilized to a reaction structure within a reaction recess of the reaction structure.

13. The device of claim 6, wherein the device circuitry of the device base forms complementary metal-oxide semiconductor (CMOS) circuits.

14. A biosensor, comprising:
    the device of claim 1; and
    a flow cell mounted to the device comprising at least one flow channel that is in fluid communication with the reaction sites to direct a reaction solution thereto.

15. A method, comprising:
    filling a plurality of trenches over a deposited support layer with a first filter material that filters light of at least a first wavelength and permits light of a second wavelength to pass therethrough to the at least one corresponding light sensor, where the plurality of trenches are within a device base comprising a plurality of light sensors;
    removing an upper portion of the deposited support layer within the plurality of trenches positioned between the device base and the first filter material to form a plurality of voids;
    filling the plurality of voids with a second filter material that filters light of at least the first wavelength and permits light of a third wavelength to pass therethrough to the at least one corresponding light sensor to form a plurality of light guides, the second filter material surrounding the first filter material; and forming a reaction structure over the device base and the plurality of light guides for containing a reaction solution and at least one reaction site that generates light of at least one of the second and third wavelengths after treatment with the reaction solution in response to incident excitation light of at least the first wavelength.

16. The method of claim 15, wherein removing the upper portion of the deposited support layer within the plurality of trenches forms a support layer portion that extends below and about a bottom portion of the plurality of trenches.

17. The method of claim 15, further comprising depositing a second liner layer over inner surfaces of the plurality of trenches and over a top surface of the device base prior to depositing the support layer such that the support layer extends over the second liner layer.

18. The method of claim 15, wherein the first filter material further filters the light of the third wavelength and wherein the second filter material further filters the light of the second wavelength.

19. The method of claim 15, wherein the first filter material is a polymer material with a first dye, and the second filter material is a polymer material with a second dye that differs from the first dye.

20. A device, comprising:
a plurality of reaction sites;
a plurality of light sensors; and
a plurality of light guides with input regions to receive incident excitation light and light emissions from at least one corresponding reaction site, the light guides extending from the input regions toward at least one corresponding light sensor, wherein each of the plurality of light guides comprise a first filter region formed of a first filter material to filter the incident excitation light of at least a first wavelength and permit the light emissions of a second wavelength to pass therethrough, and a second filter region formed of a second filter material to filter the incident excitation light of at least the first wavelength and permit the light emissions of a third wavelength to pass therethrough, wherein at least one corresponding light sensor receives the light emissions of the second wave length passing through the first filter material and receives the light emission of the third wave length passing through the second filter material.

\* \* \* \* \*